US010851423B2

(12) United States Patent
Ozers et al.

(10) Patent No.: US 10,851,423 B2
(45) Date of Patent: Dec. 1, 2020

(54) SNP ARRAYS

(71) Applicant: Proteovista LLC, Madison, WI (US)

(72) Inventors: Mary Szatkowski Ozers, Madison, WI (US); Christopher L. Warren, Madison, WI (US); Matthew J. Rodesch, Madison, WI (US)

(73) Assignee: Proteovista LLC, Madison, WI (US)

( * ) Notice: Subject to any disclaimer, the term of this patent is extended or adjusted under 35 U.S.C. 154(b) by 133 days.

(21) Appl. No.: 15/739,480

(22) PCT Filed: Jun. 20, 2016

(86) PCT No.: PCT/US2016/038399
§ 371 (c)(1),
(2) Date: Dec. 22, 2017

(87) PCT Pub. No.: WO2016/209772
PCT Pub. Date: Dec. 29, 2016

(65) Prior Publication Data
US 2018/0327850 A1    Nov. 15, 2018

Related U.S. Application Data

(60) Provisional application No. 62/182,934, filed on Jun. 22, 2015.

(51) Int. Cl.
| | | |
|---|---|---|
| *C12Q 1/6886* | (2018.01) | |
| *C07H 21/04* | (2006.01) | |
| *C07H 21/02* | (2006.01) | |
| *C12Q 1/6883* | (2018.01) | |
| *C40B 60/12* | (2006.01) | |

(52) U.S. Cl.
CPC ........... *C12Q 1/6886* (2013.01); *C07H 21/02* (2013.01); *C07H 21/04* (2013.01); *C12Q 1/6883* (2013.01); *C40B 60/12* (2013.01); *C12Q 2600/156* (2013.01)

(58) Field of Classification Search
None
See application file for complete search history.

(56) References Cited

U.S. PATENT DOCUMENTS

| | | |
|---|---|---|
| 5,010,175 A | 4/1991 | Rutter et al. |
| 5,288,514 A | 2/1994 | Ellman |
| 5,506,337 A | 4/1996 | Summerton et al. |
| 5,519,134 A | 5/1996 | Acevedo et al. |
| 5,525,735 A | 6/1996 | Gallop et al. |
| 5,549,974 A | 8/1996 | Holmes |
| 5,554,501 A | 9/1996 | Coassin et al. |
| 5,569,588 A | 10/1996 | Ashby et al. |
| 5,593,853 A | 1/1997 | Chen et al. |
| 5,866,336 A | 2/1999 | Nazarenko et al. |
| 6,001,983 A | 12/1999 | Benner |
| 6,013,789 A | 1/2000 | Rampal |

| | | | |
|---|---|---|---|
| 2009/0226912 A1* | 9/2009 | Xu | ........................ C12Q 1/6886 435/6.14 |
| 2012/0150032 A1* | 6/2012 | Gudmundsson | ..... C12Q 1/6886 600/437 |
| 2014/0057795 A1 | 2/2014 | Xu et al. | |

FOREIGN PATENT DOCUMENTS

| | | |
|---|---|---|
| WO | WO 85/01051 | 3/1985 |
| WO | WO 89/10977 | 11/1989 |
| WO | WO 91/19735 | 12/1991 |
| WO | WO 92/00091 | 1/1992 |
| WO | WO 93/20242 | 10/1993 |
| WO | WO 97/00271 | 1/1997 |

OTHER PUBLICATIONS

Olama et al Human Molecular Genetics. 2015. 24(19): 5589-5602.*
Geertz et al Briefings in Functional Genomics. 2010. 9(5): 362-373 (Year: 2010).*
Warren et al National Institutes of Health. Small Business Innovation Research Grants (SBIR)—Phase I (R43). "High Throughput Method to Assess SNP Functionality in Prostate Cancer." 2011, available via URL: < grantome.com/grant/NIH/R43-CA163405-01> (Year: 2011).*
Ahmadiyeh et al., 8q24 prostate, breast, and colon cancer risk loci show tissue-specific long-range interaction with MYC. Proc Natl Acad Sci U S A. May 25, 2010;107(21):9742-6.
Amankwah et al., Prostate cancer susceptibility polymorphism rs2660753 is not associated with invasive ovarian cancer. Cancer Epidemiol Biomarkers Prev. May 2011;20(5):1028-31.
Bigby et al., The usefulness of induced sputum in the diagnosis of Pneumocystis carinii pneumonia in patients with the acquired immunodeficiency syndrome. Am Rev Respir Dis. Apr. 1986;133(4):515-8.
Brooke et al., The role of androgen receptor mutations in prostate cancer progression. Curr Genomics. Ma. 2009;10(1):18-25.
Campbell et al., Phosphonate Ester Synthesis Using a Modified Mitsunobu Condensation. J. Org. Chem., 1994;59(3):658-660.
Carlson et al., Specificity landscapes of DNA binding molecules elucidate biological function. Proc Natl Acad Sci U S A. Mar. 9, 2010;107(10):4544-9.
Caruthers et al., Chemical synthesis of deoxyoligonucleotides by the phosphoramidite method. Methods Enzymol. 1987;154:287-313.
Chen et al., "Analogous" Organic Synthesis of Small-Compound Libraries: Validation of Combinatorial Chemistry in Small-Molecule Synthesis J. Am. Chem. Soc., 1994;116(6):2661-2.
Chen et al., NF-kappa B activates prostate-specific antigen expression and is upregulated in androgen-independent prostate cancer. Mol Cell Biol. Apr. 2002;22(8):2862-70.
Cho et al., An unnatural biopolymer. Science. Sep. 3, 1993;261(5126):1303-5.

(Continued)

*Primary Examiner* — Carla J Myers
(74) *Attorney, Agent, or Firm* — Casimir Jones, S.C.; Thomas Isenbarger

(57) ABSTRACT

Provided herein is technology relating to genetic determinants of disease and particularly, but not exclusively, to methods, compositions, and systems for identifying single nucleotide polymorphisms that are functionally associated with a disease.

16 Claims, 4 Drawing Sheets

Specification includes a Sequence Listing.

(56) References Cited

OTHER PUBLICATIONS

Clark et al., Diversity of TMPRSS2-ERG fusion transcripts in the human prostate. Oncogene. Apr. 19, 2007;26(18):2667-73.
Dewitt et al., "Diversomers": an approach to nonpeptide, nonoligomeric chemical diversity. Proc Natl Acad Sci U S A. Aug. 1, 1993;90(15):6909-13.
Dignam et al., Accurate transcription initiation by RNA polymerase II in a soluble extract from isolated mammalian nuclei. Nucleic Acids Res. Mar. 11, 1983;11(5):1475-89.
Dittrich et al., "Cut and combine": an easy membrane-supported combinatorial synthesis technique. Bioorg Med Chem Lett. Sep. 8, 1998;8(17):2351-6.
Duggan et al., Two genome-wide association studies of aggressive prostate cancer implicate putative prostate tumor suppressor gene DAB2IP. J Natl Cancer Inst. Dec. 19, 2007;99(24):1836-44.
Eeles et al., Identification of seven new prostate cancer susceptibility loci through a genome-wide association study. Nat Genet. Oct. 2009;41(10):1116-21.
Eeles et al., Multiple newly identified loci associated with prostate cancer susceptibility. Nat Genet. Mar. 2008;40(3):316-21.
El-Deiry et al., The p53MH algorithm and its application in detecting p53-responsive genes. Proc Natl Acad Sci U S A. Jun. 25, 2002;99(13):8467-72.
Frayling et al., A genetic link between type 2 diabetes and prostate cancer. Diabetologia. Oct. 2008;51(10):1757-60.
Furka et al., General method for rapid synthesis of multicomponent peptide mixtures. Int J Pept Protein Res. Jun. 1991;37(6):487-93.
Gabriel et al., The structure of haplotype blocks in the human genome. Science. Jun. 21, 2002;296(5576):2225-9.
Geysen et al., Use of peptide synthesis to probe viral antigens for epitopes to a resolution of a single amino acid. Proc Natl Acad Sci U S A. Jul. 1984;81(13):3998-4002.
Gronberg, Prostate cancer epidemiology. Lancet. Mar. 8, 2003;361(9360):859-64.
Gudmundsson et al., Common sequence variants on 2p15 and Xp11.22 confer susceptibility to prostate cancer. Nat Genet. Mar. 2008;40(3):281-3.
Gudmundsson et al., Genome-wide association study identifies a second prostate cancer susceptibility variant at 8q24. Nat Genet. May 2007;39(5):631-7.
Hagihara et al., Vinylogous polypeptides: an alternative peptide backbone. J. Am. Chem. Soc., 1992;114(16):6568-6570.
Handel et al., Integrating multiple oestrogen receptor alpha ChIP studies: overlap with disease susceptibility regions, DNase I hypersensitivity peaks and gene expression. BMC Med Genomics. Oct. 30, 2013;6:45.
Hazelett et al., Comprehensive functional annotation of 77 prostate cancer risk loci. PLoS Genet. Jan. 30, 2014;10(1):e1004102.
Hermans et al., TMPRSS2:ERG fusion by translocation or interstitial deletion is highly relevant in androgen-dependent prostate cancer, but is bypassed in late-stage androgen receptor-negative prostate cancer. Cancer Res. Nov. 15, 2006;66(22):10658-63.
Hindorff et al., Potential etiologic and functional implications of genome-wide association loci for human diseases and traits. Proc Natl Acad Sci U S A. Jun. 9, 2009;106(23):9362-7.
Hinds et al., Whole-genome patterns of common DNA variation in three human populations. Science. Feb. 18, 2005;307(5712):1072-9.
Hirschmann et al., Nonpeptidal peptidomimetics with .beta.-D-glucose scaffolding. A partial somatostatin agonist bearing a close structural relationship to a potent, selective substance P antagonist. J. Am. Chem. Soc., 1992;114(23):9217-8.
Hollstein et al., p53 mutations in human cancers. Science. Jul. 5, 1991;253(5015):49-53.
Houghton et al., Generation and use of synthetic peptide combinatorial libraries for basic research and drug discovery. Nature. Nov. 7, 1991;354(6348):84-6.
Houghton, General method for the rapid solid-phase synthesis of large numbers of peptides: specificity of antigen-antibody interaction at the level of individual amino acids. Proc Natl Aced Sci U S A. Aug. 1985;82(15):5131-5.
Hsu et al., A novel prostate cancer susceptibility locus at 19q13. Cancer Res. Apr. 1, 2009;69(7):2720-3.
International Search Report and Written Opinion for PCT/US2016/038399, dated Dec. 5, 2016, 14 pages.
Karim et al., The ETS-domain: a new DNA-binding motif that recognizes a purine-rich core DNA sequence. Genes Dev. Sep. 1990;4(9):1451-3.
Kote-Jarai et al., Multiple novel prostate cancer predisposition loci confirmed by an international study: the Practical Consortium. Cancer Epidemiol Biomarkers Prev. Aug. 2008;17(8):2052-61.
Kovacs et al., Diagnosis of Pneumocystis carinii pneumonia: improved detection in sputum with use of monoclonal antibodies. N. Engl J Med. Mar. 10, 1988;318(10):589-93.
Kruglyak et al., Variation is the spice of life. Nat Genet. Mar. 2001;27(3):234-6.
Lam et al., A new type of synthetic peptide library for identifying ligand-binding activity. Nature. Nov. 7, 1991;354(6348):82-4.
Lam et al., The "One-Bead-One-Compound" Combinatorial Library Method. Chem Rev. Apr. 1, 1997;97(2):411-448.
Lenardo et al., NF-kappa B: a pleiotropic mediator of inducible and tissue-specific gene control. Cell. Jul. 28, 1989;58(2):227-9.
Liang et al., Parallel synthesis and screening of a solid phase carbohydrate library. Science. Nov. 29, 1996;274(5292):1520-2.
Lin et al., Synthesis and duplex stability of oligonucleotides containing cytosine-thymine analogues. Nucleic Acids Res. Dec. 25, 1989;17(24):10373-83.
Lin et al., Synthesis of oligodeoxyribonucleotides containing degenerate bases and their use as primers in the polymerase chain reaction. Nucleic Acids Res. Oct. 11, 1992;20(19):5149-52.
Lou et al., Fine mapping and functional analysis of a common variant in MSMB on chromosome 10q11.2 associated with prostate cancer susceptibility. Proc Natl Acad Sci U S A. May 12, 2009;106(19):7933-8.
Lu et al., Association of prostate cancer risk with SNPs in regions containing androgen receptor binding sites captured by ChIP-On-chip analyses. Prostate. Mar. 2012;72(4):376-85.
Mariotto et al., Projections of the cost of cancer care in the United States: 2010-2020. J Natl Cancer Inst. Jan. 19, 2011;103(2):117-28.
Matson et al., Biopolymer synthesis on polypropylene supports. I. Oligonucleotides. Anal Biochem. Mar. 1994;217(2):306-10.
Ognibene et al., The diagnosis of Pneumocystis carinii pneumonia in patients with the acquired immunodeficiency syndrome using subsegmental bronchoalveolar lavage. Am Rev Respir Dis. Jun. 1984;129(6):929-32.
Ozers et al., OR51-5: SNP-SNAP Binding Arrays Reveal SNPs That Modulate Transcription Factor Interactions in Prostate Cancer. Abstract. Endocrine Society's 96th Annual Meeting and Expo, Jun. 21-24, 2014, Chicago, 2 pages.
Perkel, Life Science Technologies: Molecular Diagnostics: Personalizing Personalized Medicine. Science 2009;324:815-7.
Pomerantz et al., The 8q24 cancer risk variant rs6983267 shows long-range interaction with MYC in colorectal cancer. Nat Genet. Aug. 2009;41(8):882-4.
Reynard et al., CpG methylation regulates allelic expression of GDF5 by modulating binding of SP1 and SP3 repressor proteins to the osteoarthritis susceptibility SNP r5143383. Hum Genet. Aug. 2014;133(8):1059-73.
Roche et al., A consensus DNA-binding site for the androgen receptor. Mol Endocrinol. Dec. 1992;6(12):2229-35.
Schluger et al., Application of DNA amplification to pneumocystosis: presence of serum Pneumocystis carinii DNA during human and experimentally induced Pneumocystis carinii pneumonia. Send to J Exp Med. Nov. 1, 1992;176(5):1327-33.
Schumacher et al., Genome-wide association study identifies new prostate cancer susceptibility loci. Hum Mol Genet. Oct. 1, 2011;20(19):3867-75.
Schweitzer et al., Aromatic Nonpolar Nucleosides as Hydrophobic Isosteres of Pyrimidine and Purine Nucleosides. J Org Chem. Dec. 1, 1994;59(24):7238-7242.

(56) References Cited

OTHER PUBLICATIONS

Schweitzer et al., Hydrophobic, Non-Hydrogen-Bonding Bases and Base Pairs in DNA. J Am Chem Soc. Feb. 22, 1995;117(7):1863-1872.

Scott et al., Searching for peptide ligands with an epitope library. Science. Jul. 27, 1990;249(4967):386-90.

Siegel et al., Cancer statistics, 2014. CA Cancer J Clin. Jan.-Feb. 2014;64(1):9-29.

Songyang et al., SH2 domains recognize specific phosphopeptide sequences. Cell. Mar. 12, 1993;72(5):767-78.

Sun et al., Sequence variants at 22q13 are associated with prostate cancer risk. Cancer Res. Jan. 1, 2009;69(1):10-5.

Takata et al., Genome-wide association study identifies five new susceptibility loci for prostate cancer in the Japanese population. Nat Genet. Sep. 2010;42(9):751-4.

Taplin et al., Androgen receptor: a key molecule in the progression of prostate cancer to hormone independence. J Cell Biochem. Feb. 15, 2004;91(3):483-90.

Thomas et al., Multiple loci identified in a genome-wide association study of prostate cancer. Nat Genet. Mar. 2008;40(3):310-5.

Varghese et al., Genome-wide association studies in common cancers—what have we learnt? Curr Opin Genet Dev. Jun. 2010;20(3):201-9.

Vaughan et al., Human antibodies with sub-nanomolar affinities isolated from a large non-immunized phage display library. Nat Biotechnol. Mar. 1996;14(3):309-14.

Venter et al., The sequence of the human genome. Science. Feb. 16, 2001;291(5507):1304-51.

Wright et al., Upregulation of c-MYC in cis through a large chromatin loop linked to a cancer risk-associated single-nucleotide polymorphism in colorectal cancer cells. Mol Cell Biol. Mar. 2010;30(6):1411-20.

Yeager et al., Identification of a new prostate cancer susceptibility locus on chromosome 8q24. Nat Genet. Oct. 2009;41(10):1055-7.

\* cited by examiner

SNP ARRAYS

This application claims priority to U.S. provisional patent application Ser. No. 62/182,934, filed Jun. 22, 2015, which is incorporated herein by reference in its entirety.

STATEMENT REGARDING FEDERALLY SPONSORED RESEARCH OR DEVELOPMENT

This invention was made with government support under Grant No. 1R43CA163405-01 awarded by the National Cancer Institute Innovative Molecular Analysis Technologies (IMAT) program. The government has certain rights in the invention.

FIELD

Provided herein is technology relating to genetic determinants of disease and particularly, but not exclusively, to methods, compositions, and systems for identifying single nucleotide polymorphisms that are functionally associated with a disease.

BACKGROUND

Single nucleotide polymorphisms (SNPs) are the most abundant source of genetic variation in organisms. For example, over 100 million SNPs have been identified in the human genome (1-3). While many SNPs have been associated with disease, there is a need for technologies directed at understanding disease etiology. Such technologies will find use in improving personalized medicine (5, 6).

SUMMARY

A critical unmet need in implementing personalized medicine is the ability to sort through the millions of SNPs present in the human genome and to pinpoint which of these DNA variations are causative in disease. A key understudied function of SNPs is their ability to generate or disrupt genomic binding sites for biomolecules (e.g., proteins, metabolites, nucleic acids) that modulate gene expression, such as transcription factors involved in a disease (see, e.g., FIG. 1).

Accordingly, provided herein is a high-throughput microarray technology to evaluate SNP function in human disease (e.g., cancer, e.g., prostate cancer) (see, e.g., FIG. 2). Each probe on the microarray is displayed as double-stranded DNA matching a 25 base pair (bp) region of the genome comprising a SNP allele. For example, during the development of the technology, embodiments of the microarray were constructed that comprised approximately 400,000 DNA probes representing over 175,000 SNPs from genomic regions that were identified from genome wide association studies (GWAS) of prostate cancer. The array included allelic variations of SNPs from genomic regions that contained a GWAS SNP that demonstrated a strong statistical association with prostate cancer and/or that were predicted to affect the binding site for key transcription factors involved in prostate cancer. During the development of the technology provided herein, experiments were conducted to test the binding of transcription factors (e.g., p53, NF-kB, ERG, and androgen receptor (AR)) to the SNPs on the array. The data collected during the experiments identified several SNPs that modulated the binding affinity and/or specificity of the transcription factors tested. These candidate "functional" SNPs were subsequently analyzed to identify nearby genes, minor allele frequencies (MAFs), distance to and linkage disequilibrium with their corresponding GWAS SNPs, localization within peaks defined by previously published ChIP-Seq data, and other parameters. Additional experiments were conducted to test candidate functional SNPs that differentially bound transcription factors on the microarray. In particular, candidate functional SNPs were selected for analysis in an independent prostate cancer patient population to determine statistical association with prostate cancer incidence and/or severity.

In some embodiments, the data were analyzed using multi-dimensional analytical techniques. For example, in some embodiments, the high content data from the microarray experiments were organized to produce a "molecular signature" that related transcription factor binding (e.g., binding affinity), SNP preferences (e.g., binding specificity), and chromosomal position of nearby genes.

This technology can assay millions of SNPs and multiple transcription factors simultaneously, thus representing a novel technology to evaluate SNP functionality in a high throughput manner. While experiments were conducted to identify SNPs having a functional role in prostate cancer, the microarray technology described herein, by virtue of the microarray design and ability to examine millions of DNA permutations, is broadly applicable to any disease and disease model.

Accordingly, provided herein is a technology related to microarrays for identifying functional single nucleotide polymorphisms associated with a disease. In particular, the microarrays according to the technology comprise a plurality of features on a substrate; each feature comprises a nucleic acid probe having a sequence comprising a test single nucleotide polymorphism, wherein said test single nucleotide polymorphism is from a genome region comprising a tag single nucleotide polymorphism known to be associated with the disease. A tag single nucleotide polymorphism is a single nucleotide polymorphism having a known association with a disease. A test single nucleotide polymorphism is a single nucleotide polymorphism, in the genomic vicinity of a tag single nucleotide polymorphism, which is tested for binding to a biomolecule (e.g., a protein, e.g., a transcription factor). Furthermore, if different allelic variations of the test single nucleotide polymorphism modulate (e.g., elicit an effect on) the binding of the biomolecule then the test single nucleotide polymorphism is a functional single nucleotide polymorphism.

The technology is not limited in the number of features (e.g., addressable regions (e.g., "spots") comprising a clonal plurality of probes) on the microarrays. For example, embodiments provide arrays comprising 100 to 1,000,000 features (e.g., 100; 500; 1,000; 5,000; 10,000; 50,000; 100,000, 500,000, or 1,000,000 or more features). Further, the technology is not limited in the number of probes within each feature. For example, in some embodiments a feature comprises 100 to 10,000,000 probes (e.g., 100; 500; 1,000; 5,000; 10,000; 50,000; 100,000; 500,000; 1,000,000; 5,000,000; or 10,000,000 or more probes per feature, e.g., 100 to 10,000,000 probes having the same sequence (e.g., 100; 500; 1,000; 5,000; 10,000; 50,000; 100,000; 500,000; 1,000,000; 5,000,000; or 10,000,000 or more probes having the same sequence per feature). The microarray technology is not limited in the size of the probes. For example, in some embodiments, the nucleic acid probes comprise 10 to 500 nucleotides (e.g., 10, 15, 20, 25, 30, 35, 40, 45, 50, 55, 60, 65, 70, 75, 80, 85, 90, 100, 150, 200, 250, 300, 350, 400, 450, 500 or more nucleotides).

In preferred embodiments, the probes comprise a double stranded region. In some embodiments, the probes are hairpin probes, e.g., the nucleic acid probes comprise a double stranded and a single stranded ("loop") region. In some embodiments, the 3' or 5' end of each probe is attached to the substrate, e.g., each probe is attached to the substrate by a linker.

As described herein, probes are designed to cover genomic regions comprising one or more tag single nucleotide polymorphisms. In some embodiments, a genomic region comprising one or more tag single nucleotide polymorphisms comprises 1,000 to 1,000,000 nucleotides (e.g., 1,000; 5,000; 10,000; 50,000; 100,000; 500,000; or 1,000,000 nucleotides).

In some embodiments, the microarrays according to the technology comprise one or more sets of features corresponding to genomic regions identified as comprising one or more tag single nucleotide polymorphisms. That is, in some embodiments, a plurality of probes from the same genomic region (e.g., a genomic region associated with the same one or more tag single nucleotide polymorphisms) is provided on the microarray as a set of features. Accordingly, in some embodiments the plurality of features on the microarray comprises a set (e.g., a subset) of features, said set of features comprising nucleic acid probes comprising nucleotide sequences from the genomic region comprising the tag single nucleotide polymorphism. In some embodiments, the microarray comprises 1 to 100 sets of features, each set of features corresponding to a different genome region comprising one or more tag single nucleotide polymorphisms. In particular, embodiments provide that each feature of the set of features comprises nucleic acid probes comprising nucleotide sequences comprising a test single nucleotide polymorphism from the genomic region comprising the tag single nucleotide polymorphism. In some embodiments, the set of features comprises 1 to 1000 features, each feature comprising nucleic acid probes comprising nucleotide sequences comprising a test single nucleotide polymorphism.

In preferred embodiments, microarrays comprise multiple probes for each test single nucleotide polymorphism, e.g., in some embodiments a plurality of probes comprise genome sequences with the same test single nucleotide polymorphism present in a different location in the probe sequence (see, e.g., FIG. 3). Accordingly, the technology provides a microarray comprising a feature comprising the test single nucleotide polymorphism in the 5' third of the nucleic acid sequence of the nucleic acid probe, a feature comprising the test single nucleotide polymorphism in the center third of the nucleic acid sequence of the nucleic acid probe, and a feature comprising the test single nucleotide polymorphism in the 3' third of the nucleic acid sequence of the nucleic acid probe.

The technology is not limited in the coverage of the genome provided by the probes of the microarray. For instance, in some embodiments the microarray comprises nucleic acids comprising nucleotide sequences from approximately 1 megabase to approximately 10 megabases of the genome (e.g., approximately 1, 1.5, 2, 2.5, 3, 3.5, 4, 4.5, 5, 5.5, 6, 6.5, 7, 7.5, 8, 8.5, 9, 9.5, or 10 megabases), e.g., covering approximately 1 to 10 megabases (e.g., approximately 1, 1.5, 2, 2.5, 3, 3.5, 4, 4.5, 5, 5.5, 6, 6.5, 7, 7.5, 8, 8.5, 9, 9.5, or 10 megabases) of the genome.

The microarray finds use in identifying single nucleotide polymorphisms that bind to one or more biomolecules (e.g., proteins, e.g., transcription factors). Accordingly, in some embodiments the microarray further comprises a biomolecule bound to the nucleic acid probe having a sequence comprising the test single nucleotide polymorphism. While certain embodiments describe the technology in reference to the binding of proteins (e.g., transcription factors) to a probe, the technology is not limited to such embodiments. Thus, the technology finds use in identifying functional single nucleotide polymorphisms that bind to proteins, nucleic acids (e.g., DNA, RNA), metabolites, small molecules, drugs, etc.

As described herein, the technology comprises aspects of probe design and selection. Accordingly, methods comprise identifying a genome region comprising a tag single nucleotide polymorphism associated with a disease. Then, probes are provided comprising test single nucleotide polymorphisms from the genome region (e.g., comprising hundreds to thousands to millions of nucleotides) that are to be tested for binding to a biomolecule, thus identifying them as functional single nucleotide polymorphisms. Accordingly, such probe design and selection provides embodiments of a nucleic acid (e.g., a probe) comprising a nucleotide sequence comprising a test single nucleotide polymorphism from a genome region comprising a tag single nucleotide polymorphism. As described herein, such probes are attached to a microarray substrate. In preferred embodiments, the tag single nucleotide polymorphism is known to be associated with a disease (e.g., from previous statistical correlation (e.g., by GWAS), by previously known or suspected interaction with a biomolecule known to be associated with the disease, etc.). The tag single nucleotide polymorphism and other test single nucleotide polymorphisms in the genome region may or may not be genetically linked. Accordingly, in some embodiments the tag single nucleotide polymorphism and the test single nucleotide polymorphism are in linkage disequilibrium. In some embodiments, the tag single nucleotide polymorphism and the test single nucleotide polymorphism are not in linkage disequilibrium. In some embodiments, the tag single nucleotide polymorphism and the test single nucleotide polymorphism are not in a haploblock.

In some embodiments, the probes as described herein are hairpin probes, e.g., comprising a first duplexing region, a single stranded (e.g., loop) region, and a second duplexing region (e.g., a second duplexing region complementary to the first duplexing region) (e.g., comprising a single stranded region and a double stranded region comprising the test single nucleotide polymorphism, e.g., comprising a single stranded region in between a double stranded region comprising the test single nucleotide polymorphism). In various embodiments, the probes comprise 10 to 100 nucleotides (e.g., 10, 15, 20, 25, 30, 35, 40, 45, 50, 55, 60, 65, 70, 75, 80, 85, 90, 95, or 100 nucleotides). The probes are derived from a genome region comprising one or more tag single nucleotide polymorphisms associated with a disease. In some embodiments, the genome region comprises 100 to 1,000,000 nucleotides (e.g., 100; 500; 1,000; 5,000; 10,000; 50,000; 100,000; 500,000; or 1,000,000 nucleotides). In some embodiments, the genome region comprising the tag single nucleotide polymorphism comprises one or more test single nucleotide polymorphisms.

In some embodiments, the probes are present in one or more features comprising a clonal plurality of probe nucleic acids. For instance, some embodiments provide a microarray feature comprising 1,000 to 10,000,000 nucleic acids (e.g., 1,000; 5,000; 10,000; 50,000; 100,000; 500,000; 1,000,000; or 10,000,000 probes) comprising the same nucleotide sequence. In some embodiments, the microarray feature comprises nucleic acids linked to a substrate. Some embodiments provide one or more sets of microarray features. For example, some embodiments provide a set of microarray features such that each feature of the set comprises probes having test single nucleotide polymorphisms from the genome region comprising the tag single nucleotide polymorphism. Some embodiments provide probes that comprise the same single nucleotide polymorphism. For instance, in some embodiments the set of microarray features comprises a test single nucleotide polymorphism in the probes of at least 3 different features.

Thus, as described herein, the technology provides a nucleic acid attached to a microarray substrate, said nucleic acid comprising a nucleotide sequence from a genomic region comprising a tag single nucleotide polymorphism associated with a disease, wherein the nucleotide sequence comprises a test single nucleotide polymorphism to test for a functional association with the disease. Further embodiments provide an assay composition for identifying a functional single nucleotide polymorphism associated with a disease, the assay composition comprising the microarray as described herein and a sample comprising a biomolecule associated with the disease. The biomolecule may be present, for example and without limitation, in purified form, semi-purified form, or in a crude lysate.

The technology provided herein also relates to methods for constructing a microarray to identify functional single nucleotide polymorphisms associated with a disease, the method comprising selecting one or more tag single nucleotide polymorphisms associated with the disease; identifying test single nucleotide polymorphisms in a genome region comprising one or more tag single nucleotide polymorphisms; and linking a plurality of nucleic acid probes to a microarray substrate, each probe comprising a nucleotide sequence comprising a test single nucleotide polymorphism. The technology is not limited in the number of tag single nucleotide polymorphisms selected. For instance, embodiments provide that the selecting step comprises selecting 1 to 100 tag single nucleotide polymorphisms associated with the disease (e.g., 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 single nucleotide polymorphisms). Further, the technology is not limited by the genome region in which the tag and test single nucleotide polymorphisms reside, e.g., in some embodiments, the genome region comprises 1,000 to 1,000,000 nucleotides (e.g., 100; 500; 1,000; 5,000; 10,000; 50,000; 100,000; 500,000; or 1,000,000 nucleotides). Further, the technology is not limited in the number of genome regions in which the tag and test single nucleotide polymorphisms reside, e.g., in some embodiments the one or more tag single nucleotide polymorphisms are present in two or more genome regions.

Various criteria may be used to select the tag single nucleotide polymorphisms that find use in embodiments of methods provided herein. For instance, embodiments provide that tag single nucleotide polymorphisms are selected based on one or more of a known association with the disease; a significant statistical correlation with the disease; and/or a significantly altered allele frequency for subjects having the disease relative to a control group not having the disease. In some embodiments, the one or more tag single nucleotide polymorphisms is chosen from a genome wide association study (GWAS) of single nucleotide polymorphisms and the disease. In some embodiments, probes are designed such that each test single nucleotide polymorphism is present in at least three nucleic acid probes. Further, in some embodiments the plurality of nucleic acid probes comprises a plurality of different alleles of each test single nucleotide polymorphism. Additional embodiments provide a method for identifying a functional single nucleotide polymorphism associated with a disease, the method comprising providing a microarray comprising a plurality of nucleic acid probes, each nucleic acid probe having a nucleotide sequence comprising a test single nucleotide polymorphism from a genome region comprising a tag single nucleotide polymorphism known to be associated with the disease; contacting the microarray with a biomolecule associated with the disease; detecting modulated binding affinity and/or specificity of the biomolecule to a test single nucleotide polymorphism; and identifying the test single nucleotide polymorphism detected to have modulated binding affinity and/or specificity with the biomolecule to be a functional single nucleotide polymorphism associated with the disease. The technology is not limited in the biomolecule that is contacted to the microarray. For instance, in some embodiments, the biomolecule is a protein (e.g., a transcription factor), a nucleic acid, metabolite, or drug. Functional single nucleotide polymorphisms modulate binding of a biomolecule to a genomic sequence. Accordingly, the functional single nucleotide polymorphism may, e.g., generate, destroy, enhance, reduce, etc. a binding site in a genomic sequence. Accordingly, in some embodiments the modulated binding affinity is an increased binding affinity or a decreased binding affinity. In some embodiments, the modulated binding specificity is an increased binding specificity or a decreased binding specificity. In some embodiments, the test single nucleotide polymorphism detected to have modulated binding affinity and/or specificity with the biomolecule generates and/or disrupts a genomic binding site associated with the disease. In some embodiments, the test single nucleotide polymorphism detected to have modulated binding affinity and/or specificity with the biomolecule causes the disease.

The technology is not limited in the disease associated with the tag and/or test and/or functional single nucleotide polymorphisms. In some embodiments the disease is cancer; in some embodiments, the disease is adverse drug reactions; age-related macular degeneration and other eye disorders; aging; amyotrophic lateral sclerosis, Parkinson's disease, Alzheimer's disease, epilepsy, stroke, and other neuronal disorders; asthma and other allergic disorders; autism spectrum disorder and other cognitive developmental disorders; biomarker levels; cardiac, blood, and pulmonary disorders; cirrhosis and other liver disorders; cleft palate and other craniofacial disorders; clubfoot and other congenital disorders; depression, addiction, eating disorders, and other psychological disorders; diabetes and other metabolic disorders; hypothyroidism and other hormonal disorders; individuals susceptible to certain types of viral or bacterial infections, such as AIDS or leprosy; lupus, multiple sclerosis, and other autoimmune disorders; nephropathy and other kidney disorders; osteoporosis and other bone disorders; or any other disease with a genetic determinant.

The single nucleotide polymorphisms associated with the technology are not limited in the regions of the genome in which they are present. For example, in some embodiments the test single nucleotide polymorphism is from a non-coding region of the genome. In some embodiments, the test single nucleotide polymorphism is from a regulatory region of a genome. Further, in some embodiments the single nucleotide polymorphisms modulate binding by modulating the methylation of nucleic acid.

Further embodiments of the technology relates to a method for analyzing the interaction of a biomolecule with test single nucleotide polymorphisms in a genome, the method comprising providing a microarray comprising a plurality of nucleic acid probes, each nucleic acid probe having a nucleotide sequence comprising a test single nucleotide polymorphism from a genome region comprising a tag single nucleotide polymorphism known to be associated with the disease; contacting the microarray with a biomolecule associated with the disease; and providing a sequence specificity landscape for the biomolecule comprising probe intensity data, chromosome location data, and distances of each single nucleotide polymorphism from nearest gene.

In addition, the technology provides embodiments of a system for identifying a functional single nucleotide polymorphism associated with a disease, the system comprising a microarray comprising a plurality of nucleic acid probes, each nucleic acid probe having a nucleotide sequence comprising a test single nucleotide polymorphism from a genome region comprising a tag single nucleotide polymorphism known to be associated with the disease; and a component to detect modulated binding affinity and/or specificity of a biomolecule to a test single nucleotide polymorphism. In some embodiments, systems further comprise a computer configured to receive data describing the binding affinity and/or specificity of the biomolecule and output a sequence specificity landscape for the biomolecule comprising probe intensity data, chromosome location data, and distances of each single nucleotide polymorphism from nearest gene.

The technology finds use in identifying functional single nucleotide polymorphisms that are associated with a disease and thus that are useful in diagnosis and treatment of the disease. Accordingly, the technology provides embodiments of a nucleic acid comprising a nucleotide sequence comprising a functional single nucleotide polymorphism identified using a microarray as provided herein (or a reverse complement of a nucleotide sequence comprising a functional single nucleotide polymorphism identified using a microarray as provided herein). In some embodiments the technology provides a nucleic acid comprising a nucleotide sequence comprising a functional single nucleotide polymorphism identified by a method as described herein (or a reverse complement of a nucleotide sequence comprising a functional single nucleotide polymorphism identified by a method as described herein). In sum, the diagnostic methods provided by the technology relate to embodiments of methods for identifying a subject having a disease, the method comprising at least detecting a functional single nucleotide polymorphism associated with the disease.

Exemplary embodiments developed during the experiments described herein provide a method for identifying a subject having a prostate cancer or an increased susceptibility to prostate cancer, the method comprising detecting one or more single nucleotide polymorphism(s) selected from the group consisting of Tag_SNP1, Tag_SNP2, Tag_SNP5, Tag_SNP7, Tag_SNP9, Tag_SNP12, Tag_SNP13, Tag_SNP17, Tag_SNP18, Tag_SNP19, Tag_SNP20, Tag_SNP23, Tag_SNP26; Test_SNP1, Test_SNP2, Test_SNP3, Test_SNP8, Test_SNP10, Test_SNP11, Test_SNP12, Test_SNP13, and Test_SNP23. In some embodiments, the technology provides a method for identifying a subject having a decreased susceptibility to prostate cancer, the method comprising detecting one or more single nucleotide polymorphism(s) selected from the group consisting of Tag_SNP6, Tag_SNP11, Tag_SNP16, Tag_SNP24, and Test_SNP9. In some embodiments, the technology provides a method for identifying a subject having prostate cancer to have an increased likelihood of having a non-aggressive prostate cancer having a Gleason score of 6 or lower, the method comprising detecting one or more single nucleotide polymorphism(s) selected from the group consisting of Tag_SNP5, Tag_SNP7, Tag_SNP8, Test_SNP8, Test_SNP11, and Test_SNP23. In some embodiments, the technology provides a method for identifying a subject having prostate cancer to have an increased likelihood of having an aggressive prostate cancer having a Gleason score of 7 or higher, the method comprising detecting one or more single nucleotide polymorphism(s) selected from the group consisting of Tag_SNP4, Tag_SNP6, Tag_SNP15, Tag_SNP24, Tag_SNP26, Test_SNP9, and Test_SNP18.

The technology is not limited in the detection method used to detect binding of a biomolecule to a single nucleotide polymorphism. For instance, in some embodiments detecting one or more single nucleotide polymorphisms comprises use of a fluorescently labeled probe, nucleic acid sequencing, or polymerase chain reaction.

In some embodiments, a method comprises detecting a functional single nucleotide polymorphism in a sample from a patient. In some embodiments, detecting a functional single nucleotide polymorphism in a sample from a patient identifies the subject as having or having an increased likelihood of having a disease. In associated embodiments, methods further comprise treating the subject. In some embodiments, the subject is treated for prostate cancer. In some embodiments, methods further comprise testing the subject for the presence of a disease. In some embodiments, the subject is tested for the presence of prostate cancer. In some embodiments, the subject is treated and/or tested a second, third, or subsequent time, e.g., some embodiments further comprise testing the subject for prostate cancer and/or further comprise treating the subject for prostate cancer. Some embodiments provide a method of treating a patient identified as having a disease associated with the aberrant interaction of a biomolecule with a functional single nucleotide polymorphism, the method comprising administering to the patient a drug that modulates the interaction of the biomolecule with the functional single nucleotide polymorphism and/or that modulates the activity of the biomolecule.

Embodiments relate to functional single nucleotide polymorphisms identified herein to be associated with prostate cancer. Accordingly, some embodiments provide a nucleic acid probe for diagnosing prostate cancer that specifically hybridizes to a nucleic acid comprising a single nucleotide polymorphism selected from the group consisting of Tag_SNP1, Tag_SNP2, Tag_SNP4, Tag_SNP5, Tag_SNP6, Tag_SNP7, Tag_SNP8, Tag_SNP9, Tag_SNP11, Tag_SNP12, Tag_SNP13, Tag_SNP15, Tag_SNP16, Tag_SNP17, Tag_SNP18, Tag_SNP19, Tag_SNP20, Tag_SNP21, Tag_SNP23, Tag_SNP24, Tag_SNP26, Test_SNP1, Test_SNP2, Test_SNP3, Test_SNP8, Test_SNP9, Test_SNP10, Test_SNP11, Test_SNP12, Test_SNP13, Test_SNP18, and Test_SNP23. In some embodiments, the probe comprises a detectable label, e.g., a covalently attached detectable label.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 4 is a SNP-Sequence Specificity Landscape plot for ERG, which shows the binding specificity and affinity of ERG assessed using the SNP microarray described herein.

Figure 1:
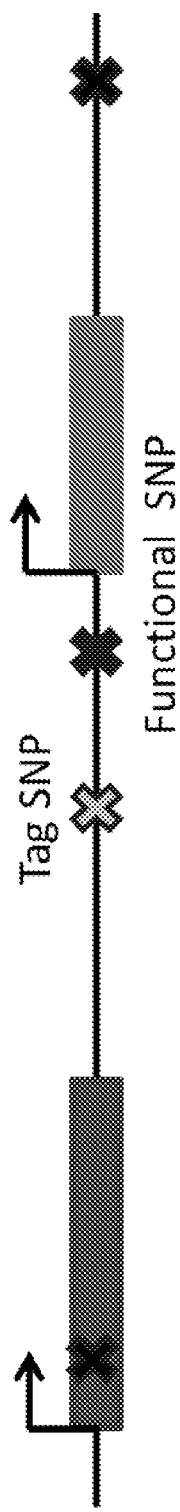
FIG. 1 is a schematic drawing showing a portion of a genome comprising various SNPs, including "tag" SNPs and "functional" SNPs. Tag SNPs (outlined "x" labeled "Tag SNP") often provide a readout in GWAS studies on all SNPs in LD (linkage disequilibrium), but the true causal SNP (filled "x" labeled "Functional SNP") may not be the same as the GWAS tag SNP.
Figure 2:
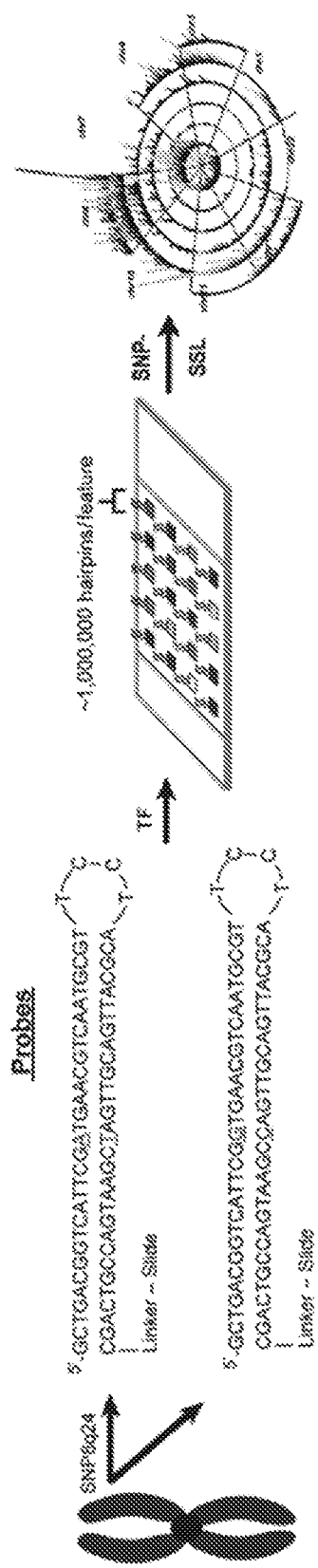
FIG. 2 is a schematic drawing showing aspects of the microarray technology. In some embodiments, every allelic variation of a SNP is displayed in a hairpin DNA probe. The array is incubated with a biomolecule (e.g., transcription factor (TF)) of interest and biomolecule binding is detected (e.g., by fluorescence). The array (zoomed in for detail) comprises hundreds of thousands to millions of unique SNP features, with thousand to millions of identical SNP hairpins per feature. The fluorescent features are identified and used to determine DNA binding preferences of SNP-binding biomolecules, e.g., by developing a multidimensional molecular signature (e.g., a "SNP Sequence Specificity Landscape" ("SNP-SSL") analysis). The top probe has a nucleotide sequence provided by SEQ ID NO: 6. The bottom probe has a nucleotide sequence provided by SEQ ID NO: 7.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology related to identifying single nucleotide polymorphisms that are functionally associated with a disease. In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein. The section headings used herein are for organizational purposes only and are not to be construed as limiting the described subject matter in any way.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the term "single nucleotide polymorphism" or "SNP" refers to single nucleotide position in a genomic sequence for which two or more alternative alleles are present at appreciable frequency (e.g., at least 0.1%) in a population.

As used herein, the term "functional single nucleotide polymorphism" refers to a single nucleotide polymorphism that generates or disrupts a binding site for a biomolecule (e.g., a protein (e.g., a transcription factor), a nucleic acid, etc.) in a genome, thus causing or ameliorating a disease or providing a readout for a disease, e.g., has a "functional association" with the disease.

As used herein, the term "tag single nucleotide polymorphism" refers to a single nucleotide polymorphism that has a positive statistical association with a disease. A tag single nucleotide polymorphism may be a functional single nucleotide polymorphism or may be associated with the disease by being linked (e.g., in linkage disequilibrium) to a functional single nucleotide polymorphism.

As used herein, the term "test single nucleotide polymorphism" refers to a single nucleotide polymorphism that is tested to determine if the test single nucleotide polymorphism is a functional single nucleotide polymorphism.

As used herein, "locus" refers to any segment of DNA sequence defined by chromosomal coordinates in a reference genome known to the art, irrespective of biological function.

A DNA locus can contain multiple genes or no genes; it can be a single base pair or millions of base pairs.

As used herein, a "polymorphic locus" is a genomic locus at which two or more alleles have been identified.

As used herein, an "allele" is one of two or more existing genetic variants of a specific polymorphic genomic locus.

As used herein, a "haplotype" is a unique set of alleles at separate loci that are observed to be inherited as a group (e.g., the alleles segregate together); alleles of a haplotype are often, but are not necessarily, grouped closely together on the same DNA molecule. A haplotype can be defined by a set of specific alleles at each defined polymorphic locus within a haploblock.

As used herein, a "haploblock" refers to a genomic region that maintains genetic integrity over multiple generations and is recognized by linkage disequilibrium within a population. Haploblocks are defined empirically for a given population of individuals. As used herein, "linkage disequilibrium" is the non-random association of alleles at two or more loci within a particular population. Linkage disequilibrium is measured as a departure from the null hypothesis of linkage equilibrium, where each allele at one locus associates randomly with each allele at a second locus in a population of individual genomes.

As used herein, a "genome" is the total genetic information carried by an individual organism or cell, represented by the complete DNA sequences of its chromosomes.

The term "minor allele", as used herein, refers to the allele that is least frequent in a defined group of individuals when compared with alternative allelic variants at the same genomic position. Minor Allele Frequency (MAF) refers to the frequency of the minor allele in the group.

As used herein, the term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses, or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups is/are replaced with halogen atoms or aliphatic groups, are functionalized as ethers, amines, or the like.

Nucleotides may include those that when incorporated into an extending strand of a nucleic acid enables continued extension (non-chain terminating nucleotides) and those that prevent subsequent extension (e.g. chain terminators). The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). Nucleotides include those nucleotides containing modified bases, modified sugar moieties, and modified phosphate backbones, for example as described in U.S. Pat. No. 5,866,336, incorporated herein by reference.

Examples of modified base moieties that can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N~6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl)uracil, and 2,6-diaminopurine amongst others.

Examples of modified sugar moieties which may be used to modify nucleotides at any position on its structure include, but are not limited to arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

The term "nucleotide analogue" as used herein refers to modified or non-naturally occurring nucleotides including but not limited to analogues that have altered stacking interactions such as 7-deaza purines (i.e., 7-deaza-dATP and 7-deaza-dGTP); base analogues with alternative hydrogen bonding configurations (e.g., such as Iso-C and Iso-G and other non-standard base pairs described in U.S. Pat. No. 6,001,983 to S. Benner and herein incorporated by reference); non-hydrogen bonding analogues (e.g., non-polar, aromatic nucleoside analogues such as 2,4-difluorotoluene, described by B. A. Schweitzer and E. T. Kool, J. Org. Chem., 1994, 59, 7238-7242, B. A. Schweitzer and E. T. Kool, J. Am. Chem. Soc., 1995, 117, 1863-1872; each of which is herein incorporated by reference); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). Nucleotide analogues include nucleotides having modification on the sugar moiety, such as dideoxy nucleotides and 2'-O-methyl nucleotides. Nucleotide analogues include modified forms of deoxyribonucleotides as well as ribonucleotides.

"Peptide nucleic acid" means a DNA mimic that incorporates a peptide-like polyamide backbone.

As used herein, the term "% sequence identity" refers to the percentage of nucleotides or nucleotide analogues in a nucleic acid sequence that is identical with the corresponding nucleotides in a reference sequence after aligning the two sequences and introducing gaps, if necessary, to achieve the maximum percent identity. Hence, in case a nucleic acid according to the technology is longer than a reference sequence, additional nucleotides in the nucleic acid, that do not align with the reference sequence, are not taken into account for determining sequence identity. Methods and computer programs for alignment are well known in the art, including blastn, Align 2, and FASTA.

The term "homology" and "homologous" refers to a degree of identity. There may be partial homology or complete homology. A partially homologous sequence is one that is less than 100% identical to another sequence.

The term "sequence variation" as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

As used herein, the terms "complementary" or "complementarity" are used in reference to polynucleotides (e.g., a sequence of nucleotides such as an oligonucleotide or a target nucleic acid) related by the base-pairing rules. For example, for the sequence "5'-A-G-T-3'" is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

In some contexts, the term "complementarity" and related terms (e.g., "complementary", "complement") refers to the nucleotides of a nucleic acid sequence that can bind to another nucleic acid sequence through hydrogen bonds, e.g., nucleotides that are capable of base pairing, e.g., by Watson-Crick base pairing or other base pairing. Nucleotides that can form base pairs, e.g., that are complementary to one another, are the pairs: cytosine and guanine, thymine and adenine, adenine and uracil, and guanine and uracil. The percentage complementarity need not be calculated over the entire length of a nucleic acid sequence. The percentage of complementarity may be limited to a specific region of which the nucleic acid sequences that are base-paired, e.g., starting from a first base-paired nucleotide and ending at a last base-paired nucleotide. The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine.

Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Thus, in some embodiments, "complementary" refers to a first nucleobase sequence that is at least 60%, 65%, 70%, 75%, 80%, 85%, 90%, 95%, 97%, 98%, or 99% identical to the complement of a second nucleobase sequence over a region of 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more nucleobases, or that the two sequences hybridize under stringent hybridization conditions. "Fully complementary" means each nucleobase of a first nucleic acid is capable of pairing with each nucleobase at a corresponding position in a second nucleic acid. For example, in certain embodiments, an oligonucleotide wherein each nucleobase has complementarity to a nucleic acid has a nucleobase sequence that is identical to the complement of the nucleic acid over a region of 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more nucleobases.

"Mismatch" means a nucleobase of a first nucleic acid that is not capable of pairing with a nucleobase at a corresponding position of a second nucleic acid.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the melting temperature (Tm) of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

The term "nucleic acid" and "polynucleotide" are used interchangeably herein to describe a polymer that can be of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902, incorporated herein by reference) and which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, uracil and thymine (G, C, A, U and T, respectively).

Further, as used herein, a "nucleic acid" (e.g., a nucleic acid molecule or sequence) is a deoxyribonucleotide or ribonucleotide polymer including without limitation, cDNA, mRNA, genomic DNA, and synthetic (such as chemically synthesized) DNA or RNA. The nucleic acid can be double-stranded (ds) or single-stranded (ss). Where single-stranded, the nucleic acid can be the sense strand or the antisense strand. Nucleic acids can include natural nucleotides (such as A, T/U, C, and G), and can also include analogs of natural nucleotides, such as labeled nucleotides. Some examples of nucleic acids include the probes disclosed herein. Unless otherwise specified, any reference to a DNA molecule is intended to include the reverse complement of that DNA molecule. DNA molecules, though written to depict only a single strand, encompass both strands of a double-stranded DNA molecule.

The term "oligonucleotide", as used herein, denotes a single-stranded multimer of nucleotides from about 2 to 500 nucleotides, e.g., 2 to 200 nucleotides. Oligonucleotides may be synthetic or may be made enzymatically, and, in some embodiments, are under 50 (e.g., under 45, 40, 35, 30, 25, 20, 15, or under 10) nucleotides in length. Oligonucleotides may contain ribonucleotide monomers (e.g., may be oligoribonucleotides) or deoxyribonucleotide monomers. Oligonucleotides may be 10 to 20, 21 to 30, 31 to 40, 41 to 50, 51 to 60, 61 to 70, 71 to 80, 81 to 100, 101 to 150, or 151 to 200, up to 500 or more nucleotides in length, for example.

The term "probe," as used herein, refers to an oligonucleotide. According to the technology provided herein, detection of a functional SNP requires detecting the binding, or detecting altered binding, e.g., due to allelic variation, of a biomolecule to a probe. In certain embodiments, a probe may be immobilized on a surface of a substrate, where the substrate can have a variety of configurations, e.g., a sheet, bead, or other structure. In certain embodiments, a probe may be present on a surface of a substantially planar substrate, e.g., in the form of a microarray.

In some embodiments, a probe is in the form of a "hairpin". As used herein, a "hairpin" is a nucleic acid structure formed from a single strand of nucleic acid that is self-complementary, that is, the nucleic acid hybridizes with itself to form a loop at one end. Thus, a hairpin comprises a double stranded region and a single stranded loop region. When the double stranded region is present in the folded hairpin, the 5' and 3' ends of the nucleic acid are proximate to one another. The linear sequence of the hairpin (e.g., in an unfolded form) comprises a first complementary region, the loop region, and a second complementary region. When the hairpin is folded, the first complementary region and the second complementary region hybridize to form the double stranded region.

As used herein, a "label" is an agent capable of detection. For example, a "label" refers in some embodiments to any atom or molecule that can be used to provide a detectable (preferably quantifiable) effect, and that can be attached to a nucleic acid or protein. Labels include, but are not limited to: radioactive isotopes, enzyme substrates, co-factors, ligands, chemiluminescent agents, fluorophores, haptens, enzymes, and combinations thereof, dyes (e.g., fluorescent dyes or moieties); particular examples include radiolabels such as $^{32}$P; binding moieties such as biotin; haptens such as digoxgenin; luminogenic, phosphorescent, or fluorogenic moieties; mass tags; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, characteristics of mass or behavior affected by mass (e.g., MALDI time-of-flight mass spectrometry; fluorescence polarization), and the like. A label may be a charged moiety (positive or negative charge) or, alternatively, may be charge neutral. Labels can include or consist of nucleic acid or protein sequence, so long as the sequence comprising the label is detectable.

For example, a label can be attached to a nucleic acid molecule (such as the probes disclosed herein) or to a protein, thereby permitting detection of the nucleic acid molecule or protein. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

In some embodiments, the label is a "fluorophore". As used herein, a "fluorophore" or "fluor" or "fluorescent molecule" and the like (e.g., "fluorescent moiety") is a compound that is excited by exposure to a particular stimulus (such as a defined "excitation" wavelength of light) and subsequently emits light (fluoresces), at a different wavelength (such as a longer "emission" wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) can eliminate the need for an external source of electromagnetic radiation, such as a laser.

Examples of particular fluorophores that can be used in the probes disclosed herein are provided in U.S. Pat. No. 5,866,366, such as 4-acetamido-4'-isothiocyanatostilbene-2, 2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4', 6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives; LightCycler Red 640; Cy5.5; and Cy56-carboxyfluorescein; 5-carboxyfluorescein (5-FAM); boron dipyrromethene difluoride (BODIPY); N,N,N',N'-tetramethyl-6-carboxyrhodamine (TAMRA); acridine, stilbene, -6-carboxy-fluorescein (HEX), TET (Tetramethyl fluorescein), 6-carboxy-X-rhodamine (ROX), Texas Red, 2',7'-dimethoxy-4',5'-dichloro-6-carboxyfluorescein (JOE), Cy3, CyS, VICO (Applied Biosystems), LC Red 640, LC Red 705, Yakima yellow amongst others.

Other suitable fluorophores include those known to those skilled in the art, for example those available from Molecular Probes (Eugene, Oreg.).

As used herein, the term "microarray" or "array" refers to a one-dimensional, two-dimensional, or three-dimensional arrangement of addressable regions ("features"), e.g., spatially addressable regions or optically addressable regions, bearing nucleic acid probes, particularly oligonucleotides or synthetic mimetics thereof. In some cases, the addressable regions of the array may not be physically connected to one another, for example, a plurality of beads that are distinguishable by optical or other means may constitute an array. Nucleic acid probes of an array may be adsorbed, physisorbed, chemisorbed, or covalently attached to the arrays at any point or points along the nucleic acid chain and may be attached to the substrate by a linker.

Arrays can be fabricated using drop deposition from pulse-jets of either precursor units (such as nucleotide monomers) in the case of in situ fabrication, or the previously obtained nucleic acid. Such methods are described, e.g., in U.S. Pat. Nos. 6,242,266; 6,232,072; 6,180,351; 6,171,797; 6,323,043; U.S. Patent Application Publication No. 20040203138, each of which is incorporated herein by reference. Also, instead of drop deposition methods, photolithographic array fabrication methods may be used. Interfeature areas need not be present particularly when the arrays are made by photolithographic methods.

Arrays may also be made by distributing pre-synthesized nucleic acids linked to beads, also termed microspheres, onto a substrate. In certain embodiments, unique optical signatures are incorporated into the beads, e.g. fluorescent dyes that are used to identify the chemical functionality on any particular bead. Since the beads are first coded with an optical signature, the array may be decoded later, such that correlation of the location of an individual site on the array with the probe at that particular site may be made after the array has been made. Such methods are described, e.g., in U.S. Pat. Nos. 6,355,431; 7,033,754; and 7,060,431, each of which is incorporated by reference in its entirety.

An array is "addressable" when it has multiple regions of different moieties (e.g., different nucleic acid probe sequences) such that a feature (i.e., an "element" or "spot" of the array) at a particular predetermined location (i.e., an "address") on the array contains one or more probes comprising the same particular sequence. Array features are typically, but need not be, separated by intervening spaces. An array is also "addressable" if the features of the array each have an optically detectable signature that identifies the moiety present at that feature. An array is also "addressable" if the features of the array each have a signature, which is detectable by non-optical means, that identifies the moiety present at that feature.

As used herein, the term "feature" refers to a defined or addressable area of a microarray comprising nucleic acid probes.

As used herein, the term "substrate" refers to material capable of supporting associated assay components (e.g., assay regions, cells, test compounds, etc.). In some embodiments, the term "substrate" refers to a material that is suitable for derivatization with a linker group. Examples of substrates include, but are not limited to glass, Si-based materials, functionalized polystyrene, functionalized polyethyleneglycol, functionalized organic polymers, nitrocellulose or nylon membranes, paper, cotton, and materials suitable for synthesis. Substrates need not be flat and include any type of shape including spherical shapes (e.g., beads). Materials attached to a substrate may be attached to any portion of the substrate (e.g., may be attached to an interior portion of a porous substrate material). Preferred embodiments of the present technology have nucleic acid probes attached to a substrate. A nucleic acid probe is "attached" to a substrate when it is associated with the substrate through a non-random chemical or physical interaction. In some preferred embodiments, the attachment is through a covalent bond, e.g., as provided by a linker.

As used herein, the term "linker" refers to a chemical moiety that is attachable to a substrate on one end and a nucleic acid probe on the other end. The "linker" comprises atoms or molecules that link or bond two entities (e.g., substrate and nucleic acid probe), but that is not a part of either of the individual linked entities.

The terms "determining", "measuring", "evaluating", "assessing," "assaying," and "analyzing" are used interchangeably herein to refer to any form of measurement and include determining if an element is present or not. These terms include both quantitative and/or qualitative determinations. Assessing may be relative or absolute. "Assessing the presence of" includes determining the amount of something present, as well as determining whether it is present or absent.

The term "corresponding" is a relative term indicating similarity in position, purpose, or structure. For example, a nucleic acid sequence corresponding to a gene promoter indicates that the nucleic acid sequence is similar to the promoter found in an organism; a nucleic acid sequence corresponding to a genome region indicates that the nucleic acid sequence is similar to the sequence found in the genome region found in an organism.

As used herein, the terms "subject" and "patient" refer to any organisms including plants, microorganisms, and animals (e.g., mammals such as dogs, cats, livestock, and humans).

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin.

As used herein, a "biological sample" refers to a sample of biological tissue or fluid. For instance, a biological sample may be a sample obtained from an animal (including a human); a fluid, solid, or tissue sample; as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagomorphs, rodents, etc. Examples of biological samples include sections of tissues, blood, blood fractions, plasma, serum, urine, or samples from other peripheral sources or cell cultures, cell colonies, single cells, or a collection of single cells. Furthermore, a biological sample includes pools or mixtures of the above mentioned samples. A biological sample may be provided by removing a sample of cells from a subject, but can also be provided by using a previously isolated sample. For example, a tissue sample can be removed from a subject suspected of having a disease by conventional biopsy techniques. In some embodiments, a blood sample is taken from a subject. A biological sample from a patient means a sample from a subject suspected to be affected by a disease.

Environmental samples include environmental material such as surface matter, soil, water, and industrial samples, as well as samples obtained from food and dairy processing instruments, apparatus, equipment, utensils, disposable and non-disposable items. These examples are not to be construed as limiting the sample types applicable to the present invention.

As used herein, a "transcription factor" is a protein that regulates transcription. In particular, transcription factors regulate the binding of RNA polymerase and the initiation of transcription. A transcription factor binds upstream or downstream to either enhance or repress transcription of a gene by assisting or blocking RNA polymerase binding. The term transcription factor includes both inactive and activated transcription factors.

Transcription factors are typically modular proteins that affect regulation of gene expression. Exemplary transcription factors include but are not limited to AAF, ab1, ADA2, ADA-NF1, AF-1, AFP1, AhR, AIIN3, ALL-1, alpha-CBF, alpha-CP1, alpha-CP2a, alpha-CP2b, alphaHo, alphaH2-alphaH3, Alx-4, aMEF-2, AML1, AML1a, AML1b, AML1c, AML1DeltaN, AML2, AML3, AML3a, AML3b, AMY-1L, A-Myb, ANF, AP-1, AP-2alphaA, AP-2alphaB, AP-2beta, AP-2gamma, AP-3 (1), AP-3 (2), AP-4, AP-5, APC, AR, AREB6, Arnt, Arnt (774 M form), ARP-1, ATBF1-A, ATBF1-B, ATF, ATF-1, ATF-2, ATF-3, ATF-3deltaZIP, ATF-a, ATF-adelta, ATPF1, Barhl1, Barhl2, Barx1, Barx2, Bcl-3, BCL-6, BD73, beta-catenin, Bin1, B-Myb, BP1, BP2, brahma, BRCA1, Brn-3a, Brn-3b, Brn-4, BTEB, BTEB2, B-TFIID, C/EBPalpha, C/EBPbeta, C/EBPdelta, CAC-Cbinding factor, Cart-1, CBF (4), CBF (5), CBP, CCAAT-binding factor, CCMT-binding factor, CCF, CCG1, CCK-1a, CCK-1b, CD28RC, cdk2, cdk9, Cdx-1, CDX2, Cdx-4, CFF, Chx10, CLIM1, CLIM2, CNBP, CoS, COUP, CP1, CP1A, CP1C, CP2, CPBP, CPE binding protein, CREB, CREB-2, CRE-BP1, CRE-BPa, CREMalpha, CRF, Crx, CSBP-1, CTCF, CTF, CTF-1, CTF-2, CTF-3, CTF-5, CTF-7, CUP, CUTL1, Cx, cyclin A, cyclin T1, cyclin T2, cyclin T2a, cyclin T2b, DAP, DAX1, DB1, DBF4, DBP, DbpA, DbpAv, DbpB, DDB, DDB-1, DDB-2, DEF, deltaCREB, deltaMax, DF-1, DF-2, DF-3, Dlx-1, Dlx-2, Dlx-3, DIx4 (long isoform), Dlx-4 (short isoform, Dlx-5, Dlx-6, DP-1, DP-2, DSIF, DSIF-p14, DSIF-p160, DTF, DUX1, DUX2, DUX3, DUX4, E, E12, E2F, E2F+E4, E2F+p107, E2F-1, E2F-2, E2F-3, E2F-4, E2F-5, E2F-6, E47, E4BP4, E4F, E4F1, E4TF2, EAR2, EBP-80, EC2, EF1, EF-C, EGR1, EGR2, EGR3, EIIaE-A, EIIaE-B, EIIaE-Calpha, EIIaE-Cbeta, EivF, EIf-1, EIk-1, Emx-1, Emx-2, Emx-2, En-1, En-2, ENH-bind. prot., ENKTF-1, EPAS1, epsilonF1, ER, Erg-1, Erg-2, ERR1, ERR2, ETF, Ets-1, Ets-1 deltaVil, Ets-2, Evx-1, F2F, factor 2, Factor name, FBP, f-EBP, FKBP59, FKHL18, FKHRL1P2, Fli-1, Fos, FOXB1, FOXC1, FOXC2, FOXD1, FOXD2, FOXD3, FOXD4, FOXE1, FOXE3, FOXF1, FOXF2, FOXG1a, FOXG1b, FOXG1c, FOXH1, FOXI1, FOXJ1a, FOXJ1b, FOXJ2 (long isoform), FOXJ2 (short isoform), FOXJ3, FOXK1a, FOXK1b, FOXK1c, FOXL1, FOXM1a, FOXM1b, FOXM1c, FOXN1, FOXN2, FOXN3, FOX01a, FOX01b, FOXO2, FOXO3a, FOXO3b, FOXO4, FOXP1, FOXP3, Fra-1, Fra-2, FTF, FTS, G factor, G6 factor, GABP, GABP-alpha, GABP-beta1, GABP-beta2, GADD 153, GAF, gammaCMT, gammaCAC1, gammaCAC2, GATA-1, GATA-2, GATA-3, GATA-4, GATA-5, GATA-6, Gbx-1, Gbx-2, GCF, GCMa, GCNS, GF1, GLI, GLI3, GR alpha, GR beta, GRF-1, Gsc, Gscl, GT-IC, GT-IIA, GT-IIBalpha, GT-IIBbeta, H1TF1, H1TF2, H2RIIBP, H4TF-1, H4TF-2, HAND1, HAND2, HB9, HDAC1, HDAC2, HDAC3, hDaxx, heat-induced factor, HEB, HEB1-p67, HEB1-p94, HEF-1B, HEF-1T, HEF-4C, HEN1, HEN2, Hesxl, Hex, HIF-1, HIF-1alpha, HIF-1beta, HiNF-A, HiNF-B, HINF-C, HINF-D, HiNF-D3, HiNF-E, HiNF-P, HIP1, HIV-EP2, Hlf, HLTF, HLTF (Met123), HLX, HMBP, HMG I, HMG I(Y), HMG Y, HMGI-C, HNF-1A, HNF-1B, HNF-1C, HNF-3, HNF-3alpha, HNF-3beta, HNF-3gamma, HNF4, HNF-4alpha, HNF4alpha1, HNF-4alpha2, HNF-4alpha3, HNF-4alpha4, HNF4gamma, HNF-6alpha, hnRNP K, HOX11, HOXA1, HOXA10, HOXA10 PL2, HOXA11, HOXA13, HOXA2, HOXA3, HOXA4, HOXA5, HOXA6, HOXA7, HOXA9A, HOXA9B, HOXB-1, HOXB13, HOXB2, HOXB3, HOXB4, HOXB5, HOXB6, HOXA5, HOXB7, HOXB8, HOXB9, HOXC10, HOXC11, HOXC12, HOXC13, HOXC4, HOXC5, HOXC6, HOXC8, HOXC9, HOXD10, HOXD11, HOXD12, HOXD13, HOXD3, HOXD4, HOXD8, HOXD9, Hp55, Hp65, HPX42B, HrpF, HSF, HSF1 (long), HSF1 (short), HSF2, hsp56, Hsp90, IBP-1, ICER-II, ICER-ligamma, ICSBP, Id1, Id1 H', Id2, Id3, Id3/Heir-1, IF1, IgPE-1, IgPE-2, IgPE-3, IkappaB, IkappaB-alpha, IkappaB-beta, IkappaBR, II-1 RF, IL-6 RE-BP, 11-6 RF, INSAF, IPF1, IRF-1, IRF-2, ir1B, IRX2a, Irx-3, Irx-4, ISGF-1, ISGF-3, ISGF3alpha, ISGF-3gamma, 1st-1, ITF, ITF-1, ITF-2, JRF, Jun, JunB, JunD, kappay factor, KBP-1, KER1, KER-1, Kox1, KRF-1, Ku autoantigen, KUP, LBP-1, LBP-1a, LBX1, LCR-F1, LEF-1, LEF-1B, LF-A1, LHX1, LHX2, LHX3a, LHX3b, LHXS, LHX6.1a, LHX6.1b, LIT-1, Lmo1, Lmo2, LMX1A, LMX1B, L-My1 (long form), L-My1 (short form), L-My2, LSF, LXRalpha, LyF-1, LyI-1, M factor, Mad1, MASH-1, Max1, Max2, MAZ, MAZ1, MB67, MBF1, MBF2, MBF3, MBP-1 (1), MBP-1 (2), MBP-2, MDBP, MEF-2, MEF-2B, MEF-2C (433 AA form), MEF-2C (465 AA form), MEF-2C (473 M form), MEF-2C/delta32 (441 AA form), MEF-2D00, MEF-2D0B, MEF-2DA0, MEF-2DA'0, MEF-2DAB, MEF-2DA'B, Meis-1, Meis-2a, Meis-2b, Meis-2c, Meis-2d, Meis-2e, Meis3, Meox1, Meox1a, Meox2, MHox (K-2), Mi, MIF-1, Miz-1, MM-1, MOPS, MR, Msx-1, Msx-2, MTB-Zf, MTF-1, mtTF1, Mxi1, Myb, Myc, Myc 1, Myf-3, Myf-4, Myf-5, Myf-6, MyoD, MZF-1, NC1, NC2, NCX, NELF, NER1, Net, NF III-a, NF NF NF-1, NF-1A, NF-1B, NF-1X, NF-4FA, NF-4FB, NF-4FC, NF-A, NF-AB, NFAT-1, NF-AT3, NF-Atc, NF-Atp, NF-Atx, NfbetaA, NF-CLE0a, NF-CLE0b, NFdeltaE3A, NFdeltaE3B, NFdeltaE3C, NFdeltaE4A, NFdeltaE4B, NFdeltaE4C, Nfe, NF-E, NF-E2, NF-E2 p45, NF-E3, NFE-6, NF-Gma, NF-GMb, NF-IL-2A, NF-IL-2B, NF-jun, NF-kappaB, NF-kappaB(-like), NF-kappaB1, NF-kappaB1, precursor, NF-kappaB2, NF-kappaB2 (p49), NF-kappaB2 precursor, NF-kappaE1, NF-kappaE2, NF-kappaE3, NF-MHCIIA, NF-MHCIIB, NF-muE1, NF-muE2, NF-muE3, NF-S, NF-X, NF-X1, NF-X2, NF-X3, NF-Xc, NF-YA, NF-Zc, NF-Zz, NHP-1, NHP-2, NHP3, NHP4, NKX2-5, NKX2B, NKX2C, NKX2G, NKX3A, NKX3A v1, NKX3A v2, NKX3A v3, NKX3A v4, NKX3B, NKX6A, Nmi, N-Myc, N-Oct-2alpha, N-Oct-2 beta, N-Oct-3, N-Oct-4, N-Oct-5a, N-Oct-5b, NP-TCII, NR2E3, NR4A2, Nrfl, Nrf-1, Nrf2, NRF-2beta1, NRF-2gamma1, NRL, NRSF form 1, NRSF form 2, NTF, 02, OCA-B, Oct-1, Oct-2, Oct-2.1, Oct-2B, Oct-2C, Oct-4A, Oct4B, Oct-5, Oct-6, Octa-factor, octamer-binding factor, oct-B2, oct-B3, Otx1, Otx2, OZF, p107, p130, p28 modulator, p300, p38erg, p45, p49erg,-p53, p55, p55erg, p65delta, p67, Pax-1, Pax-2, Pax-3, Pax-3A, Pax-3B, Pax-4, Pax-5, Pax-6, Pax-6/Pd-5a, Pax-7, Pax-8, Pax-8a, Pax-8 b, Pax-8c, Pax-8d, Pax-8e, Pax-8f, Pax-9, Pbx-1a, Pbx-1b, Pbx-2, Pbx-1a, Pbx-1b, PC2, PC4, PC5, PEA3, PEBP2alpha, PEBP2beta, Pit-1, PITX1, PITX2, PITX3, PKNOX1, PLZF, PO-B, Pontin52, PPARalpha, PPARbeta, PPARgamma1, PPARgamma2, PPUR, PR, PR A, pRb, PRD1-BF1, PRDI-BFc, Prop-1, PSE1, P-TEFb, PTF, PTFalpha, PTFbeta, PTFdelta, PTFgamma, Pu box binding factor, Pu box binding factor (BJA-B), PU.1, PuF, Pur factor, R1, R2, RAR-alpha1, RAR-beta, RAR-beta2, RAR-gamma, RAR-gamma1, RBP60, RBP-Jkappa, Rel, RelA, RelB, RFX, RFX1, RFX2, RFX3, RFXS, RF-Y, RORalpha1, RORalpha2, RORalpha3, RORbeta, ROR-gamma, Rox, RPF1, RPGalpha, RREB-1, RSRFC4, RSRFC9, RVF, RXR-alpha, RXR-beta, SAP-1a, SAP1b, SF-1, SHOX2a, SHOX2b, SHOXa, SHOXb, SHP, SIII-p110, SIII-p15, SIII-p18, SIM', Six-1, Six-2, Six-3, Six-4, Six-5, Six-6, SMAD-1, SMAD-2, SMAD-3, SMAD-4, SMAD-5, SOX-11, SOX-12, Sox-4, Sox-5, SOX-9, Sp1, Sp2, Sp3, Sp4, Sph factor, Spi-B, SPIN, SRCAP, SREBP-1a, SREBP-1b, SREBP-1c, SREBP-2, SRE-ZBP, SRF, SRY, SRP1, Staf-50, STAT1alpha, STAT1beta, STAT2, STAT3, STAT4, STAT6, T3R, T3R-alpha1, T3R-alpha2, T3R-beta, TAF(I)110, TAF(I)48, TAF(I)63, TAF(II)100, TAF(II)125, TAF(II)135, TAF(II)170, TAF(II)18, TAF(II)20, TAF(II) 250, TAF(II)250Delta, TAF(II)28, TAF(II)30, TAF(II)31, TAF(II)55, TAF(II)70-alpha, TAF(II)70-beta, TAF(II)70-gamma, TAF-I, TAF-II, TAF-L, Tal-1, Tal-1beta, Tal-2, TAR factor, TBP, TBX1A, TBX1B, TBX2, TBX4, TBXS (long isoform), TBXS (short isoform), TCF, TCF-1, TCF-1A, TCF-1B, TCF-1C, TCF-1D, TCF-1E, TCF-1F, TCF-1G, TCF-2alpha, TCF-3, TCF-4, TCF-4(K), TCF-4B, TCF-4E, TCFbeta1, TEF-1, TEF-2, tel, TFE3, TFEB, TFIIA, TFIIA-alpha/beta precursor, TFIIA-alpha/beta precursor, TFIIA-gamma, TFIIB, TFIID, TFIIE, TFIIE-alpha, TFIIE-beta, TFIIF, TFIIF-alpha, TFIIF-beta, TFIIH, TFIIH*, TFIIH-CAK, TFIIH-cyclin H, TFIIH-ERCC2/CAK, TFIIH-MAT1, TFIIH-MO15, TFIIH-p34, TFIIH-p44, TFIIH-p62, TFIIH-p80, TFIIH-p90, TFII-I, Tf-LF1, Tf-LF2, TGIF, TGIF2, TGT3, THRA1, TIF2, TLE1, TLX3, TMF, TR2, TR2-11, TR2-9, TR3, TR4, TRAP, TREB-1, TREB-2, TREB-3, TREF1, TREF2, TRF (2), TTF-1, TXRE BP, TxREF, UBF, UBP-1, UEF-1, UEF-2, UEF-3, UEF-4, USF1, USF2, USF2b, Vav, Vax-2, VDR, vHNF-1A, vHNF-1B, vHNF-1C, VITF, WSTF, WT1, WT1I, WT1 I-KTS, WT1 I-de12, WT1-KTS, WT1-de12, X2BP, XBP-1, XW-V, XX, YAF2, YB-1, YEBP, YY1, ZEB, ZF1, ZF2, ZFX, ZHX1, ZIC2, ZID, ZNF174, amongst others.

DESCRIPTION

Provided herein is technology related to identifying single nucleotide polymorphisms that are functionally associated with a disease. In particular, the technology provides a microarray comprising over 175,000 SNPs associated with prostate cancer. The microarray and multidimensional analysis described herein provide a high-throughput platform to identify functional SNPs near tag SNPs. Experiments conducted during the development of embodiments of the technology identified the differential binding of AR, NF-kB, ERG, and p53 to allelic variations of several SNPs related to prostate cancer. As a result, twenty-five SNPs were selected for further genotyping in a prostate cancer patient and control population, and data collected indicated that some of these SNPs are predictive of prostate cancer incidence and aggressiveness. Although the disclosure herein refers to certain illustrated embodiments, it is to be understood that these embodiments are presented by way of example and not by way of limitation.

Arrays

In some embodiments the technology provides an array (e.g., a microarray) comprising a plurality of features, e.g., comprising a plurality of probes comprising single nucleotide polymorphisms (SNPs) to test for interaction with a biomolecule (e.g., a protein, e.g., a transcription factor). As used herein, single nucleotide polymorphisms to which a biomolecule (e.g., a protein, e.g., a transcription factor) binds is a "functional single nucleotide polymorphism".

The arrays disclosed herein are arrangements of addressable locations ("features") on a substrate, with each feature containing a nucleic acid (e.g., a plurality of clonal nucleic acids), such as probes. In some embodiments, each feature corresponds to a single type or class of nucleic acid, such as a plurality of probes comprising the same nucleic acid sequence (e.g., comprising the same single nucleotide polymorphism), though a particular probe may be redundantly contained at multiple features. Arrays according to the technology comprise 1,000 to 1,000,000 features, e.g., more than 1,000; more than 2,000; more than 3,000; more than 4,000; more than 5,000; more than 6,000; more than 7,000; more than 8,000; more than 9,000; more than 10,000; more than 15,000; more than 20,000; more than 50,000; more than 100,000; more than 250,000; more than 500,000; more than 750,000; or more than 1,000,000 features. Features comprise 1,000 to 1,000,000 nucleic acid probes, e.g., more than 1,000; more than 2,000; more than 3,000; more than 4,000; more than 5,000; more than 6,000; more than 7,000; more than 8,000; more than 9,000; more than 10,000; more than 15,000; more than 20,000; more than 50,000; more than 100,000; more than 250,000; more than 500,000; more than 750,000; or more than 1,000,000 nucleic acid probes having the same sequence. Probes comprise about 10 to about 100 nucleotides, e.g., more than 5, more than 10, more than 15, more than 20, more than 25, more than 30, more than 40, more than 50, more than 60, more than 70, more than 80, more than 90, or about or more than 100 nucleotides. In some embodiments, probes comprise approximately 50 to 60 (e.g., 53) nucleotides.

A "microarray" is a miniaturized array that is typically examined using an imaging (e.g., microscopic imaging and/or analysis) technique for detection of binding and/or interaction. The addresses and associated features may be labeled, keyed to a separate guide, or otherwise identified by location Within an array, each arrayed nucleic acid is addressable, such that its location may be reliably and consistently determined within the at least two dimensions of the array surface. Thus, ordered arrays allow assignment of the location of each nucleic acid at the time it is placed within the array. Usually, an array map or key is provided to correlate each address with the appropriate nucleic acid. Ordered arrays are often arranged in a symmetrical grid pattern, but probes could be arranged in other patterns (for example, in radially distributed lines, a "spokes and wheel" pattern, or ordered clusters). Addressable arrays can be computer readable; a computer can be programmed to correlate a particular address on the array with information about the sample at that position, such as binding data, including signal intensity, and/or other data (e.g., related to a Sequence Specificity Landscape analysis). In some exemplary computer readable formats, the individual samples or molecules in the array are arranged regularly (for example, in a Cartesian grid pattern), which can be correlated to address information by a computer.

A feature within the array may be of any suitable shape and size, e.g., typically square or rectangular. However, in some embodiments, features are regions that are essentially triangular, oval, circular, or irregular. In some embodiments, the nucleic acids are suspended in a liquid medium and contained within square or rectangular wells on the array substrate. The overall shape of the array itself also may vary, though in some embodiments it is substantially flat and rectangular, square, or even substantial circular (such as ovoid) in shape.

In some embodiments, an array is formed on a substrate, e.g., a solid support formed from an organic polymer. Suitable materials for the solid support include, but are not limited to: polypropylene, polyethylene, polybutylene, polyisobutylene, polybutadiene, polyisoprene, polyvinylpyrrolidine, polytetrafluroethylene, polyvinylidene difluoride, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567). Other examples of suitable substrates for the arrays disclosed herein include glass (such as functionalized glass), Si, Ge, GaAs, GaP, $SiO_2$, $SiN_4$, modified silicon nitrocellulose, polystyrene, polycarbonate, nylon, fiber, or combinations thereof. Array substrates can be stiff and relatively inflexible (for example glass or a supported membrane) or flexible (such as a polymer membrane).

In general, suitable characteristics of the material that can be used to form the solid support substrate surface include: being amenable to surface activation such that upon activation, the surface of the support is capable of covalently attaching a biomolecule, such as an oligonucleotide thereto; amenability to "in situ" synthesis of biomolecules; being chemically inert such that at the areas on the support not occupied by the oligonucleotides are not amenable to non-specific binding, or when non-specific binding occurs, such materials can be readily removed from the surface without removing the oligonucleotides.

In one example, the solid support surface is polypropylene. Polypropylene is chemically inert and hydrophobic. Non-specific binding is generally avoidable, and detection sensitivity is improved. Polypropylene has good chemical resistance to a variety of organic acids (such as formic acid), organic agents (such as acetone or ethanol), bases (such as sodium hydroxide), salts (such as sodium chloride), oxidizing agents (such as peracetic acid), and mineral acids (such as hydrochloric acid). Polypropylene also provides a low fluorescence background, which minimizes background interference and increases the sensitivity of the signal of interest.

In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

A wide variety of array formats can be employed in accordance with the present disclosure. One example includes a linear array of probes, generally referred to in the art as a dipstick. Another suitable format includes a two-dimensional pattern of discrete cells or features (such as $N^2$ squares in a N×N array). As is appreciated by those skilled in the art, other array formats including, but not limited to slot (rectangular) and circular arrays are equally suitable for use (see for example U.S. Pat. No. 5,981,185). In one example, the array is formed on a polymer medium, which is a thread, membrane, or film. An example of an organic polymer medium is a polypropylene sheet having a thickness on the order of about 1 mil (0.001 inch) to about 20 mil, although the thickness of the film is not critical and can be varied over a fairly broad range.

The array formats of the present technology can be included in a variety of different types of formats. A "format" includes any format to which the solid support can be affixed, such as microtiter plates, slides, test tubes, inorganic sheets, dipsticks, and the like. For example, polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, probes are synthesized separately and then attached to a solid support (see for example U.S. Pat. No. 6,013,789, which is incorporated herein by reference). In another example, probes are synthesized directly onto the support to provide the desired array (see for example U.S. Pat. No. 5,554,501, which is incorporated herein by reference). Suitable methods for covalently coupling probes to a solid support and for directly synthesizing the oligonucleotides on the support are known to those working in the field; a summary of suitable methods can be found in Matson et al., Anal. Biochem. 217:306-10, 1994. In one example, the probes are synthesized onto the support using conventional chemical techniques for preparing oligonucleotides on solid supports (such as PCT applications WO 85/01051 and WO 89/10977, or U.S. Pat. No. 5,554,501, each of which is incorporated herein by reference).

Methods for the synthesis of oligonucleotides are well known to those of ordinary skill in the art; such methods can be used to produce probes for the disclosed methods. The most common method for in vitro oligonucleotide synthesis is the phosphoramidite method, formulated by Letsinger and further developed by Caruthers (Caruthers et al., Chemical synthesis of deoxyoligonucleotides, in Methods Enzymol. 154:287-313, 1987). See also, Gait (Ed.), Oligonucleotide Synthesis. A practical approach, IRL Press, 1984. Oligonucleotide synthesizers that employ this or similar methods are available commercially (for example, the PolyPlex oligonucleotide synthesizer from Gene Machines, San Carlos, Calif.). In addition, many companies will perform such synthesis (for example, Sigma-Genosys, The Woodlands, Tex.; Qiagen Operon, Alameda, Calif.; Integrated DNA Technologies, Coralville, Iowa; and TriLink BioTechnologies, San Diego, Calif.).

A suitable array can be produced using automated means to synthesize probes on the array by laying down the precursors for the four bases in a predetermined pattern. Briefly, a multiple-channel automated chemical delivery system is employed to create probe populations in parallel rows (corresponding in number to the number of channels in the delivery system) across the substrate. Following completion of oligonucleotide synthesis in a first direction, the substrate can then be rotated by 90° to permit synthesis to proceed within a second set of rows that are now perpendicular to the first set. This process creates a multiple-channel array whose intersection generates a plurality of discrete features.

The probes can be bound to the polypropylene support by either the 3' end of the oligonucleotide or by the 5' end of the oligonucleotide. In one example, the probes are bound to the solid support by the 3' end. However, one of skill in the art can determine whether the use of the 3' end or the 5' end of the probe is suitable for bonding to the solid support.

In some embodiments, the probes on the array include one or more labels that permit detection of binding of biomolecules to the probes.

The arrays herein can be described by their densities (the number of features in a certain specified surface area). In preferred embodiments related to microarrays, array density will usually be one or more features per square centimeter, for instance, about 1000 to 1,000,000, or more features per square centimeter. For example, in some embodiments the arrays comprise features at a density of approximately 100,000 (e.g., 80,000) features per square centimeter, e.g., on an array having an area of approximately 10 to 100 square centimeters.

However, features in an array can be of a relatively large size, such as large enough to permit detection of a signal without the assistance of a microscope or other equipment. Thus, in embodiments related to macroarrays, array density can be about one address per square decimeter (or one address in a 10 cm by 10 cm region of the array substrate) to about 50 addresses per square centimeter (50 targets within a 1 cm by 1 cm region of the substrate).

The use of the term "array" includes the arrays found in DNA microchip technology. As one, non-limiting example, the probes are contained on a DNA microchip similar to the GENECHIP® products and related products commercially available from Affymetrix, Inc. (Santa Clara, Calif.). Briefly, a DNA microchip includes a miniaturized, high-density array of probes on a glass wafer substrate.

Particular probes are selected, and photolithographic masks are designed for use in a process based on solid-phase chemical synthesis and photolithographic fabrication techniques similar to those used in the semiconductor industry. The masks are used to isolate chip exposure sites, and probes are chemically synthesized at these sites, with each probe in an identified location within the array. The probe or the biomolecule within the sample can be labeled, such as with a fluorescent label and, after binding, the binding signals can be detected and analyzed.

Methods for labeling biomolecules (e.g., nucleic acid molecules and proteins) so that they can be detected are well known. Examples of such labels include non-radiolabels and radiolabels. Non-radiolabels include, but are not limited to enzymes, chemiluminescent compounds, fluorophores, metal complexes, haptens, colorimetric agents, dyes, or combinations thereof. Radiolabels include, but are not limited to, $^{125}$I and $^{35}$S. Radioactive and fluorescent labeling methods, as well as other methods known in the art, are suitable for use with the present disclosure.

The binding conditions are selected to permit discrimination between bound and unbound biomolecules. Binding conditions can be chosen to correspond to those known to be suitable in standard procedures for binding of biomolecules to nucleic acids and then optimized for use with the arrays provided herein. For example, conditions suitable for binding of one type of target would be adjusted for the use of other targets for the array. In particular, temperature is controlled to minimize and/or eliminate non-specific association of biomolecules to the probes and/or substrate. A variety of known binding media can be employed, the choice being dependent on considerations known to one of skill in the art.

Once the biomolecules have been bound to the probes present in the array, the presence of the bound complex can be analyzed, for example by detecting the complexes.

Detecting a bound complex in an array of oligonucleotide probes comprises detection of one or more labels present on the probes, the biomolecule (e.g., protein, e.g., transcription factor), or both. In some embodiments, detection includes applying a buffer. In some embodiments the buffer comprises HEPES and/or Tris; KCl, NaCl, and/or $MgCl_2$; glycerol, other components, or combinations thereof. However, other suitable buffer solutions can also be used.

Probe Design and Selection

A particular aspect of the technology provided herein relates to the selection of probes and probe sequences for the microarrays described. In particular, single nucleotide polymorphisms of interest (e.g., tag single nucleotide polymorphisms associated with a disease) are first identified. For example, single nucleotide polymorphisms may be chosen that demonstrated strong statistical association with a disease of interest and/or that were predicted to affect the binding site for biomolecules (e.g., transcription factors) associated with the disease of interest.

In some embodiments, single nucleotide polymorphisms (e.g., tag single nucleotide polymorphisms) are identified by GWAS or other association mapping studies relating one or more single nucleotide polymorphisms to a disease of interest. In some embodiments, single nucleotide polymorphisms are chosen based on information available in published reports of single nucleotide polymorphisms associated with a disease. In some embodiments, single nucleotide polymorphisms are chosen based on information available in a single nucleotide polymorphism database, e.g., the dbSNP database provided by the National Human Genome Research Institute and The National Center for Biotechnology Information. The dbSNP database was established to serve as a central repository for both single base nucleotide substitutions and short deletion and insertion polymorphisms. In some embodiments, single nucleotide polymorphisms are selected from the National Human Genome Research Institute Catalog of Published Genome-Wide Association Studies. See, e.g., Hindorff et al. (2009), *Proc Natl Acad Sci USA* 106(23): 9362-9367.

After identifying one or more single nucleotide polymorphisms (e.g., tag single nucleotide polymorphisms) associated with a disease of interest, genome regions comprising the single nucleotide polymorphisms are identified. Typically, the genome region comprising the one or more single nucleotide polymorphisms (e.g., one or more tag single nucleotide polymorphisms) includes up to approximately 1,000,000 nucleotides of a genome, e.g., up to approximately 500,000; approximately 100,000; approximately 50,000; or approximately 10,000 nucleotides of flanking sequence on each side of the identified single nucleotide polymorphisms (e.g., the tag single nucleotide polymorphisms).

After identifying genome regions comprising one or more tag single nucleotide polymorphisms, all other single nucleotide polymorphisms in the genome region are identified. That is, the genome regions are selected to comprise the tag single nucleotide polymorphisms and some amount of flanking genome sequence. Then, the genome regions are examined for the presence of other single nucleotide polymorphisms. For example, in some embodiments the one or more other single nucleotide polymorphism alleles in a genome region around the tag single nucleotide polymorphisms is/are identified using the same or similar resources as are used to identify the tag single nucleotide polymorphisms. The tag single nucleotide polymorphisms and other single nucleotide polymorphisms in the genome region provide a collection of test single nucleotide polymorphisms to test, e.g., to assess for having a functional role according to the technology provided herein.

Figure 3:
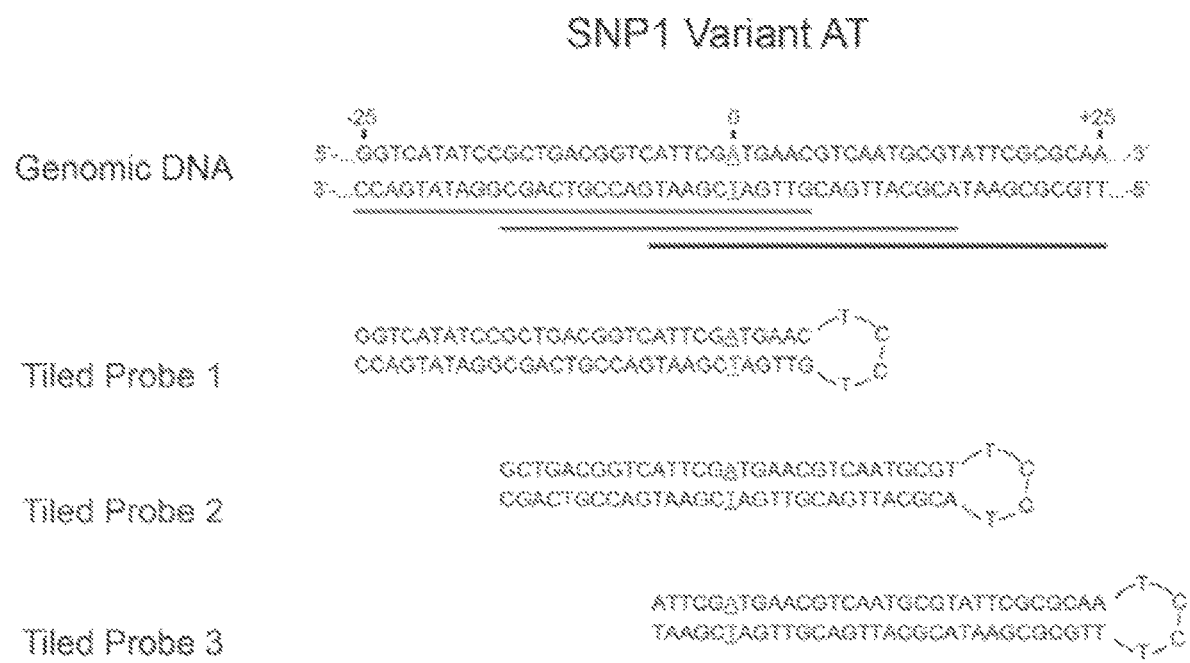
FIG. 3 is a schematic drawing showing embodiments of probes and methods of probe design described herein. In the exemplary embodiment shown, probes comprise 53 nucleotides, of which 25 nucleotides are base-paired to form a double stranded duplex region. To minimize and/or eliminate positional effects of the single nucleotide polymorphisms on the tiled probes, each single nucleotide polymorphism is represented by three probes, wherein the single nucleotide polymorphism allele is located towards the left, middle, or right of the 25-bp probe. The Genomic DNA sequence has a top strand comprising a nucleotide sequence provided by SEQ ID NO: 8 and a complementary bottom strand comprising a nucleotide sequence provided by SEQ ID NO: 9. Tiled Probe 1 has a nucleotide sequence provide by SEQ ID NO: 10. Tiled Probe 2 has a nucleotide sequence provided by SEQ ID NO: 11. Tiled Probe 3 has a nucleotide sequence provided by SEQ ID NO: 12.

To test the test single nucleotide polymorphisms, probes comprising sequences of all single nucleotide polymorphism alleles in the genome region (e.g., all test single nucleotide polymorphisms in the genome region) are synthesized and deposited (e.g., linked) to the array substrate. In some embodiments, each allele of each single nucleotide polymorphism is represented by, e.g., 3 probes, wherein the single nucleotide polymorphism allele is located towards the left, middle, or right of the probe (FIG. 3).

Further, single nucleotide polymorphisms are often clustered within a genome such that multiple single nucleotide polymorphisms are within a small genomic region approximately the size of a probe as described herein (e.g., 10 to 1000 nucleotides). Thus, in some embodiments, a probe comprising one single nucleotide polymorphism to be evaluated also comprises multiple neighboring single nucleotide polymorphisms. Accordingly, probes were provided to assess the multiple neighboring single nucleotide polymorphisms by calculating the number of allelic variations encompassed by the probe and designing multiple probes as needed to achieve coverage of all allelic permutations. For example, if a probe comprised N additional neighboring single nucleotide polymorphisms in addition to the primary single nucleotide polymorphism to be tested by the probe (N+1 total single nucleotide polymorphisms), and each single nucleotide polymorphism had X alleles, $X^{N+1}$ array probes were generated based on that core probe to provide a probe for each combination of the X alleles at the N+1 sites. In preferred embodiments, probes were designed to comprise up to seven permuted single nucleotide polymorphisms on a given core probe. In cases where there were more than six additional neighboring single nucleotide polymorphisms near the primary single nucleotide polymorphism, only the six single nucleotide polymorphisms closest to the primary single nucleotide polymorphism were permuted. The rest of the single nucleotide polymorphisms on the probe were kept the same as in the reference genome.

Samples

Appropriate samples for use in the technologies provided herein include any conventional biological sample. Samples include those obtained from, excreted by or secreted by any living organism, such as a prokaryotic organism or a eukaryotic organism including without limitation, multicellular organisms (such as plants and animals, including samples from a healthy or apparently healthy human subject or a human patient affected by a condition or disease to be diagnosed or investigated, such as cancer), clinical samples obtained from a human or veterinary subject, for instance blood or blood-fractions, biopsied tissue. Standard techniques for acquisition of such samples are available. See, for example Schluger et al., J. Exp. Med. 176:1327-33 (1992); Bigby et al., Am. Rev. Respir. Dis. 133:515-18 (1986); Kovacs et al., NEJM 318:589-93 (1988); and Ognibene et al., Am. Rev. Respir. Dis. 129:929-32 (1984). Biological samples can be obtained from any organ or tissue (including a biopsy or autopsy specimen, such as a tumor biopsy) or can comprise a cell (whether a primary cell or cultured cell) or medium conditioned by any cell, tissue or organ. In some embodiments, a biological sample is a nuclear extract. Nuclear extract contains many of the proteins contained in the nucleus of a cell, and includes for example transcription factors. Methods for obtaining a nuclear extract are well known in the art and can be found for example in Dignam, Nucleic Acids Res., 11(5):1475-89 1983.

In some embodiments, proteins are isolated from a biological sample containing a variety of other components, such as nucleic acids, lipids, and other proteins. Proteins can be obtained from any material (e.g., cellular material (live or dead), extracellular material, viral material, environmental samples, obtained from an animal, plant, bacterium, archaeon, fungus, or any other organism. In some embodiments, the biological samples for use in the present technology include viral particles or preparations thereof. Proteins can be obtained directly from an organism or from a biological sample obtained from an organism, e.g., from blood, urine, cerebrospinal fluid, seminal fluid, saliva, sputum, stool, hair, sweat, tears, skin, and tissue. Exemplary samples include, but are not limited to, whole blood, lymphatic fluid, serum, plasma, buccal cells, sweat, tears, saliva, sputum, hair, skin, biopsy, cerebrospinal fluid (CSF), amniotic fluid, seminal fluid, vaginal excretions, serous fluid, synovial fluid, pericardial fluid, peritoneal fluid, pleural fluid, transudates, exudates, cystic fluid, bile, urine, gastric fluids, intestinal fluids, fecal samples, and swabs, aspirates (e.g., bone marrow, fine needle, etc.), washes (e.g., oral, nasopharyngeal, bronchial, bronchialalveolar, optic, rectal, intestinal, vaginal, epidermal, etc.), and/or other specimens.

Any tissue or body fluid specimen may be used as a source for proteins for use in the technology, including forensic specimens, archived specimens, preserved specimens, and/or specimens stored for long periods of time, e.g., fresh-frozen, methanol/acetic acid fixed, or formalin-fixed paraffin embedded (FFPE) specimens and samples. Proteins can also be isolated from cultured cells, such as a primary cell culture or a cell line. The cells or tissues from which proteins are obtained can be infected with a virus or other intracellular pathogen. A sample can also be total protein extracted from a biological specimen.

Proteins, peptides, and polypeptides can be obtained, e.g., by extraction from a biological sample, e.g., by a variety of techniques such as those described by Maniatis, et al. (1982) Molecular Cloning: A Laboratory Manual, Cold Spring Harbor, N.Y. (see, e.g., pp. 280-281).

Screening for Modulators of Binding to Functional Single Nucleotide Polymorphisms Because of the biological importance of the binding of biomolecules to functional single nucleotide polymorphisms (such as the binding of transcription factors to single nucleotide polymorphisms), the functional single nucleotide polymorphisms and the biomolecules to which they bind represent potential targets for therapies, such as drug therapies. The methods disclosed herein can be used to identify agents that modulate the activity of one or more biomolecules that bind to functional single nucleotide polymorphisms, such as proteins, such as transcription factors, for example several different transcription factors. For example, the disclosed methods can be used to screen chemical libraries for agents that modulate the binding affinity and/or specificity of one or more of several different transcription factors. In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

Appropriate agents can be contained in libraries, for example, synthetic or natural compounds in a combinatorial library. Numerous libraries are commercially available or can be readily produced; means for random and directed synthesis of a wide variety of organic compounds and biomolecules, including expression of randomized oligonucleotides, such as antisense oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds.

Preparation and screening of combinatorial libraries is well known to those of skill in the art. Libraries (such as combinatorial chemical libraries) useful in the disclosed methods include, but are not limited to, peptide libraries (see, e.g., U.S. Pat. No. 5,010,175; Furka, Int. J. Pept. Prot. Res., 37:487-493, 1991; Houghton et al., Nature, 354:84-88, 1991; PCT Publication No. WO 91/19735), (see, e.g., Lam et al., Nature, 354:82-84, 1991; Houghten et al., Nature, 354:84-86, 1991), and combinatorial chemistry-derived molecular library made of D- and/or L-configuration amino acids, phosphopeptides (including, but not limited to, members of random or partially degenerate, directed phosphopeptide libraries; see, e.g., Songyang et al., Cell, 72:767-778, 1993), antibodies (including, but not limited to, polyclonal, monoclonal, humanized, anti-idiotypic, chimeric or single chain antibodies, and Fab, F(ab')2 and Fab expression library fragments, and epitope-binding fragments thereof), small organic or inorganic molecules (such as, so-called natural products or members of chemical combinatorial libraries), molecular complexes (such as protein complexes), or nucleic acids, encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Natl. Acad. Sci. USA, 90:6909-6913, 1993), vinylogous polypeptides (Hagihara et al., J. Am. Chem. Soc., 114:6568, 1992), nonpeptidal peptidomimetics with glucose scaffolding (Hirschmann et al., J. Am. Chem. Soc., 114:9217-9218, 1992), analogous organic syntheses of small compound libraries (Chen et al., J. Am. Chem. Soc., 116:2661, 1994), oligocarbamates (Cho et al., Science, 261:1303, 1003), and/or peptidyl phosphonates (Campbell et al., J. Org. Chem., 59:658, 1994), nucleic acid libraries (see Sambrook et al. Molecular Cloning, A Laboratory Manual, Cold Springs Harbor Press, N.Y., 1989; Ausubel et al., Current Protocols in Molecular Biology, Green Publishing Associates and Wiley Interscience, N.Y., 1989), peptide nucleic acid libraries (see, e.g., U.S. Pat. No. 5,539,083), antibody libraries (see, e.g., Vaughn et al., Nat. Biotechnol., 14:309-314, 1996; PCT App. No. PCT/US96/10287), carbohydrate libraries (see, e.g., Liang et al., Science, 274:1520-1522, 1996; U.S. Pat. No. 5,593,853), small organic molecule libraries (see, e.g., benzodiazepines, Baum, C&EN, January 18, page 33, 1993; isoprenoids, U.S. Pat. No. 5,569,588; thiazolidionones and methathiazones, U.S. Pat. No. 5,549, 974; pyrrolidines, U.S. Pat. Nos. 5,525,735 and 5,519,134; morpholino compounds, U.S. Pat. No. 5,506,337; benzodiazepines, U.S. Pat. No. 5,288,514) and the like.

Libraries useful for the disclosed screening methods can be produced in a variety of manners including, but not limited to, spatially arrayed multipin peptide synthesis (Geysen, et al., Proc. Natl. Acad. Sci., 81(13):3998-4002, 1984), "tea bag" peptide synthesis (Houghten, Proc. Natl. Acad. Sci., 82(15):5131-5135, 1985), phage display (Scott and Smith, Science, 249:386-390, 1990), spot or disc synthesis (Dittrich et al., Bioorg. Med. Chem. Lett., 8(17):2351-2356, 1998), or split and mix solid phase synthesis on beads (Furka et al., Int. J. Pept. Protein Res., 37(0487-493, 1991; Lam et al., Chem. Rev., 97(2):411-448, 1997).

Devices for the preparation of combinatorial libraries are also commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, for example, ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Libraries can include a varying number of compositions (members), such as up to about 100 members, such as up to about 1000 members, such as up to about 5000 members, such as up to about 10,000 members, such as up to about 100,000 members, such as up to about 500,000 members, or even more than 500,000 members.

In one example, the methods can involve providing a combinatorial chemical or peptide library containing a large number of potential therapeutic compounds. Such combinatorial libraries are then screened by the methods disclosed herein to identify those library members (particularly chemical species or subclasses) that display a desired characteristic activity, e.g., modulating the binding of a biomolecule to a functional single nucleotide polymorphism.

The compounds identified using the methods disclosed herein can serve as conventional "lead compounds" or can themselves be used as potential or actual therapeutics. In some instances, pools of candidate agents can be identified and further screened to determine which individual or sub-pools of agents in the collective have a desired activity.

Compounds identified by the disclosed methods can be used as therapeutics or lead compounds for drug development for a variety of conditions. Because gene expression is fundamental in all biological processes, including cell division, growth, replication, differentiation, repair, infection of cells, etc., the ability to monitor the binding of biomolecules to functional single nucleotide polymorphisms and identify compounds which modulate binding can be used to identify drug leads for a variety of conditions, including neoplasia, inflammation, allergic hypersensitivity, metabolic disease, genetic disease, viral infection, bacterial infection, fungal infection, or the like.

In some embodiments, compounds are administered to a subject (e.g., a mammal, e.g., a human). In some embodiments, a subject is tested to assess the presence, the absence, or the level of a disease, e.g., by assaying or measuring a functional single nucleotide polymorphism and/or the interaction of a biomolecule (e.g., a protein, e.g., a transcription factor) with a functional single nucleotide polymorphism, to determine the risk of or the presence of the disease, and thereafter the subject is treated with a compound (e.g., a drug or other bioactive substance) based on the outcome of the test. In some embodiments, a patient is tested, treated, and then tested again to monitor the response to therapy. In some embodiments, cycles of testing and treatment may occur without limitation to the pattern of testing and treating (e.g., test/treat, test/treat/test, test/treat/test/treat, test/treat/test/treat/test, test/treat/treat/test/treat/treat, etc), the periodicity, or the duration of the interval between each testing and treatment phase.

Systems

In some embodiments, the technology is related to systems for identifying functional single nucleotide polymorphisms. Systems according to the technology comprise, e.g., a microarray, a computer (e.g., comprising a microprocessor), and software. Some embodiments further comprise a fluorescence microscope comprising an illumination configuration to excite a fluorophore, a confocal laser scanning microscope, and the like. Some embodiments comprise a fluorescence detector, e.g., a detector comprising an intensified charge coupled device (ICCD), an electron-multiplying charge coupled device (EM-CCD), a complementary metal-oxide-semiconductor (CMOS), a photomultiplier tube (PMT), an avalanche photodiode (APD), and/or another detector capable of detecting fluorescence emission, e.g., from single chromophores. Some embodiments comprise a computer and software encoding instructions for the computer to perform.

For example, in some embodiments, computer-based analysis software is used to analyze data generated by the detection assay (e.g., the binding affinity and/or specificity of a biomolecule (e.g., a protein, e.g., a transcription factor) for a single nucleotide polymorphism) into a multidimensional binding signature. In some embodiments, data is transformed into data of predictive value for a clinician. The clinician can access the predictive data using any suitable means.

For instance, some embodiments comprise a computer system upon which embodiments of the present technology may be implemented. In various embodiments, a computer system includes a bus or other communication mechanism for communicating information and a processor coupled with the bus for processing information. In various embodiments, the computer system includes a memory, which can be a random access memory (RAM) or other dynamic storage device, coupled to the bus, and instructions to be executed by the processor. Memory also can be used for storing temporary variables or other intermediate information during execution of instructions to be executed by the processor. In various embodiments, the computer system can further include a read only memory (ROM) or other static storage device coupled to the bus for storing static information and instructions for the processor. A storage device, such as a magnetic disk or optical disk, can be provided and coupled to the bus for storing information and instructions.

In various embodiments, the computer system is coupled via the bus to a display, such as a cathode ray tube (CRT) or a liquid crystal display (LCD), for displaying information to a computer user. An input device, including alphanumeric and other keys, can be coupled to the bus for communicating information and command selections to the processor. Another type of user input device is a cursor control, such as a mouse, a trackball, or cursor direction keys for communicating direction information and command selections to the processor and for controlling cursor movement on the display. This input device typically has two degrees of freedom in two axes, a first axis (e.g., x) and a second axis (e.g., y), that allows the device to specify positions in a plane.

A computer system can perform embodiments of the present technology. Consistent with certain implementations of the present technology, results can be provided by the computer system in response to the processor executing one or more sequences of one or more instructions contained in the memory. Such instructions can be read into the memory from another computer-readable medium, such as a storage device. Execution of the sequences of instructions contained in the memory can cause the processor to perform the methods described herein. Alternatively, hard-wired circuitry can be used in place of or in combination with software instructions to implement the present teachings. Thus, implementations of the present technology are not limited to any specific combination of hardware circuitry and software.

The term "computer-readable medium" as used herein refers to any media that participates in providing instructions to the processor for execution. Such a medium can take many forms, including but not limited to, non-volatile media, volatile media, and transmission media. Examples of non-volatile media can include, but are not limited to, optical or magnetic disks, such as a storage device. Examples of volatile media can include, but are not limited to, dynamic memory. Examples of transmission media can include, but are not limited to, coaxial cables, copper wire, and fiber optics, including the wires that comprise the bus.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

Various forms of computer readable media can be involved in carrying one or more sequences of one or more instructions to the processor for execution. For example, the instructions can initially be carried on the magnetic disk of a remote computer. The remote computer can load the instructions into its dynamic memory and send the instructions over a network connection (e.g., a LAN, a WAN, the internet, a telephone line). A local computer system can receive the data and transmit it to the bus. The bus can carry the data to the memory, from which the processor retrieves and executes the instructions. The instructions received by the memory may optionally be stored on a storage device either before or after execution by the processor.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In accordance with such a computer system, some embodiments of the technology provided herein further comprise functionalities for collecting, storing, and/or analyzing data (e.g., binding affinity and/or binding specificity of a biomolecule for a single nucleotide polymorphism). For example, some embodiments contemplate a system that comprises a processor, a memory, and/or a database for, e.g., storing and executing instructions, analyzing fluorescence image data, performing calculations using the data, transforming the data, and storing the data. It some embodiments, an algorithm applies a statistical model to the data.

Many diagnostics involve determining the presence of one of more single nucleotide polymorphisms (e.g., one or more functional single nucleotide polymorphisms), the binding affinity of one or more single nucleotide polymorphisms (e.g., one or more functional single nucleotide polymorphisms), and/or the binding specificity of one or more single nucleotide polymorphisms (e.g., one or more functional single nucleotide polymorphisms). Thus, in some embodiments, an equation comprising variables representing the presence, absence, binding affinity, and/or binding specificity of one or more single nucleotide polymorphisms (e.g., one or more functional single nucleotide polymorphisms) produces a value that finds use in making a diagnosis or assessing the presence or qualities of a nucleic acid. As such, in some embodiments this value is presented by a device, e.g., by an indicator related to the result (e.g., an LED, an icon on a display, a sound, or the like). In some embodiments, a device stores the value, transmits the value, or uses the value for additional calculations.

Thus, in some embodiments, the present technology provides the further benefit that a clinician, who is not likely to be trained in genetics or molecular biology, need not understand the raw data. The data are presented directly to the clinician in its most useful form. The clinician is then able to utilize the information to optimize the care of a subject. The present invention contemplates any method capable of receiving, processing, and transmitting the information to and from laboratories conducting the assays, information providers, medical personal, and/or subjects. For example, in some embodiments of the present technology, a sample is obtained from a subject and submitted to a profiling service (e.g., a clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center or subjects may collect the sample themselves and directly send it to a profiling center. Where the sample comprises previously determined biological information, the information may be directly sent to the profiling service by the subject (e.g., an information card containing the information may be scanned by a computer and the data transmitted to a computer of the profiling center using electronic communication systems). Once received by the profiling service, the sample is processed and a profile is produced that is specific for the diagnostic or prognostic information desired for the subject. The profile data are then prepared in a format suitable for interpretation by a treating clinician. For example, rather than providing raw expression data, the prepared format may represent a diagnosis or risk assessment for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor. In some embodiments, the information is first analyzed at the point of care or at a regional facility. The raw data are then sent to a central processing facility for further analysis and/or to convert the raw data to information useful for a clinician or patient. The central processing facility provides the advantage of privacy (all data are stored in a central facility with uniform security protocols), speed, and uniformity of data analysis. The central processing facility can then control the fate of the data following treatment of the subject. For example, using an electronic communication system, the central facility can provide data to the clinician, the subject, or researchers. In some embodiments, the subject is able to access the data using the electronic communication system. The subject may chose further intervention or counseling based on the results. In some embodiments, the data are used for research use. For example, the data may be used to further optimize the inclusion or elimination of markers as useful indicators of a particular condition associated with the disease.

EXAMPLES

During the development of embodiments of the technology described herein, experiments were conducted to design and test the microarray technology provided herein. In particular, a microarray was designed and constructed to comprise probes comprising approximately a quarter-million SNPs that are associated with prostate cancer. Further, data were collected in experiments that tested the DNA binding specificity and affinity of five prostate cancer-related transcription factors as purified proteins and in cell lysates. The data collected identified allelic variations of SNPs that modulated (e.g., altered) transcription factor binding. Finally, SNP data obtained from patients with prostate cancer indicated that there is a statistically significant association of functional SNPs with prostate cancer incidence and aggressiveness.

Example 1—Design and Synthesis of a SNP Microarray

GWAS studies have identified genomic regions associated with an increased risk of prostate cancer. However, it has been difficult to identify specific variants that are causative for disease (7-11). Two particular limitations of GWAS technologies are related to the large quantity of SNPs within the genome (e.g., approximately one SNP every 300 bp) and the propensity of SNPs to co-segregate in LD with many other nearby SNPs (12, 13).

Previous efforts to solve these problems have included functionally validating small sets of interesting SNPs from regions identified by GWAS. However, this approach is not amenable to a high throughput format (14-18). In addition, previous research has indicated that SNPs involved in causing or ameliorating disease often alter transcription factor binding, e.g., leading to changes in regulation of downstream genes. (7). One example supporting this mechanism includes an 8q24 variant in a mutation hotspot associated with breast, colorectal, and prostate cancer that alters binding of TCF and in turn regulates c-Myc via long-range interactions (14-16). A second example is the variant rs10993994 on 10q that alters CREB binding and affects expression of MSMB, encoding β-microseminoprotein involved in prostate cancer (17). Additional examples are rs4907792 on chromosome X that affects an androgen response element (ARE) and rs10486567 on chromosome 7 that modulates Nkx3-1 and FoxA1 binding in androgen-stimulated enhancer activity (18). Accordingly, experiments were conducted during the development of embodiments of the technology to construct a microarray comprising tiled double-stranded DNA probes from genomic regions identified by GWAS as containing prostate cancer-associated SNPs and use this microarray to evaluate differences in transcription factor affinity due to allelic variations of the SNPs.

The microarray was successfully designed to comprise 385,000 DNA probes representing all SNPs within +/−75 kb of 12 tag SNP regions identified from GWAS studies, with a minimum coverage of 150 kb for each genomic region (see, e.g., Table 1). The SNPs were chosen based on the following criteria: 1) multiple notations in the literature; 2) strong statistical association with prostate cancer; 3) strong odds ratio. Four of these SNP regions comprise a single GWAS tag SNP; therefore the microarray covers a 150 kb region comprising and surrounding each of these four tag SNPs (19-21). Eight of these GWAS tag SNP regions comprise multiple GWAS tag SNPs that are located near each other, as reported by different GWAS studies (19-32). To provide genome regions that include these SNPs+/−75 kb on both sides of the regions comprising the SNPs, these eight regions range from 162 kb to 596 kb in genomic coverage on the microarray. Two additional negative control regions were selected: 1) 150 kb of a randomly selected genomic region with no known association with prostate cancer; and 2)+/−75 kb around a SNP strongly associated with the unrelated disease diabetes. In total, this microarray covers approximately 3 megabases (MB) of the genome.

TABLE 1 prostate cancer associated GWAS regions included on the array

| Genomic Position | GWAS SNP(s) | Chr | Chromosomal Positions | SNP Range + 150kb | # of Probes |
|---|---|---|---|---|---|
| 3p12.1-2 | rs2660753, rs9284813, rs7629490 | chr3 | 87,110,673 - 87,241,496 | 280,823 | 27,734 |
| 4q22.3 | rs12500426, rs17021918 | chr4 | 95,514,608 - 95,562,876 | 198,268 | 21,286 |
| 7q21.3 | rs6465657 | chr7 | 97,816,326 | 150,000 | 21,101 |
| 8p21.2 | rs2928679, rs1512268, rs4872176, rs1567669 | chr8 | 23,438,874 - 23,538,532 | 249,658 | 38,800 |
| 8q24.21 | rs1016343, rs13252298, rs7841060, rs1456315, rs16901979, rs16902094, rs445114, rs620861, rs6983267, rs1447295, rs4242382, rs4242384, rs7837688 | chr8 | 128,093,296 - 128,539,359 | 596,063 | 79,119 |
| 10q11.23 | rs10993994 | chr10 | 51,549,495 | 150,000 | 18,474 |
| 11q13.2 | rs12418451, rs7931342, rs10896449, rs7130881 | chr11 | 68,935,418 - 68,995,957 | 210,539 | 32,069 |
| 11p15.5 | rs7127900 | chr11 | 2,233,573 | 150,000 | 25,858 |
| 17q21.2 | rs11649743, rs4430796, rs7501939 | chr17 | 36,074,978 - 36,101,155 | 176,177 | 20,207 |
| 17q25.1 | rs1859962 | chr17 | 69,108,752 | 150,000 | 19,467 |
| 22q13.2 | rs5759167, rs742134 | chr22 | 43,500,211 - 43,518,274 | 168,063 | 33,154 |
| Xp11.22 | rs5945572, rs5945619 | chrX | 51,229,682 - 51,241,671 | 161,989 | 8,813 |
| | Random Control | chr7 | 100,000,000 | 150,000 | 13,439 |
| | r55215(Diabetes SNP) | chr11 | 17,408,629 | 150,000 | 20,277 |
| Total | | | | 2,941,580 | 379,798 |

A challenge associated with the probe design for the microarray is the high number of SNPs (approximately 40%) that are within 20 bp of the closest SNP, e.g., by analysis of the approximately 50 million SNPs in the SNP database dbSNP at the time the array was designed (3). Two elements of probe design were developed to address this challenge in the present technology. First, each allele of each SNP is represented by three core probes, wherein the SNP allele is located towards the left, middle, or right of the 25 bp probe (FIG. 3). Second, the challenge of evaluating multiple neighboring SNPs in a non-biased fashion was addressed by calculating the number of allelic variations encompassed by a 25 bp probe and designing multiple probes as needed to achieve coverage of all allelic permutations. For example, if a core probe comprised five additional neighboring SNPs in addition to the primary SNP to be tested by the probe (six total SNPs), and each SNP had two alleles, 64 array probes ($2^6$) were generated based on that core probe to provide a probe for each combination of the two alleles at the six sites. Probes were designed to comprise up to seven permuted SNPs on a given core probe. In cases where there were more than six additional neighboring SNPs near the primary SNP, only the six SNPs closest to the primary SNP were permuted. The rest of the SNPs on the probe were kept the same as in the reference genome (e.g., human reference genome hg19). The probe design process was further complicated by discrepancies between the positions assigned to each SNP by the SNP database dbSNP and the positions for the SNPs identified in the reference genome. Further, in some instances the surrounding sequence provided for each SNP in the SNP database dbSNP did not always align to the reference genome. Therefore, each SNP was aligned to the reference genome so that the position of each SNP relative to each other SNP was correct. SNPs that could not be aligned to the reference genome or that aligned to multiple positions in the reference genome were removed. Finally, in some cases single nucleotide polymorphisms were found at two or more consecutive base positions in the sequence. In these cases, polymorphisms of up to 5 bp were allowed (e.g., ACACA vs. CGCGC; or AAAAA vs. deletion, etc.). However, polymorphisms larger than 5 bp were removed due to their complexity.

In sum, during the development of embodiments of the technology provided herein, a microarray was constructed that tiles SNPs from genomic regions associated with an increased risk of prostate cancer. The microarray comprised a quarter-million different SNPs with 6 tiled probes per SNP. The microarray comprised over 175,000 SNPs and spanned 3 Mbp of the human genome.

Example 2—Test Binding Specificity of Prostate Cancer Related Transcription Factors During the development of embodiments of the technology provided herein, experiments were conducted to determine the effect of all SNPs from genomic regions containing prostate cancer-associated SNPs on transcription factor binding affinity and specificity. In particular, assays examined the binding of transcription factors known to be involved with prostate cancer signaling, including androgen receptor (AR), p53, nuclear factor kappa-light-chain-enhancer of activated B cells (NF-kB), myc, TCF4, ERG, and Stat3.

Figure 4:
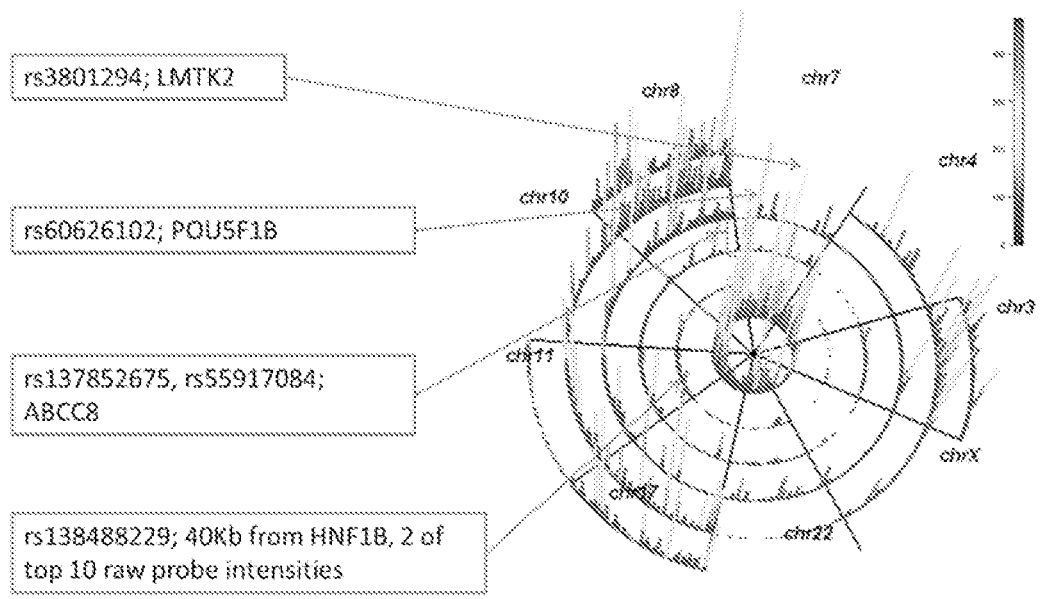
FIG. 4 shows a multidimensional "signature" for the transcription factor ERG. In particular.

Binding specificity and affinity of the transcription factors was assessed using the SNP microarray described herein and the data were analyzed by constructing a multidimensional "signature" for each transcription factor ("SNP-Sequence Specificity Landscape" ("SNP-SSL")). See, e.g., FIG. 4. In particular, a new algorithm based on a previously developed sequence specificity landscape analysis (33) was constructed to address the specific needs of the SNP binding experiments described herein. SNP-SSL provides a three-dimensional visualization of all 385,000 SNP probes on the microarray, showing individual probe intensity, chromosome location, and distance from the gene nearest the SNP. Each probe is represented by a single peak, with peak height corresponding to normalized probe fluorescence intensity, which is indicative of and proportional to binding affinity (e.g., as expressed by Ka) of the transcription factor to the probe. Additionally, probes are color coded based on a global minimum/maximum of the entire dataset. Concentric rings represent the distance of each SNP probe from the transcription start site (TSS) of the nearest gene (either upstream or downstream). Distances from TSS are binned by login, thus probes in the central ring are adjacent to the TSS, probes on the first ring are within 100 bp of the TSS, probes on the second ring are within 1000 bp of the TSS, probes on the third ring are within 10,000 bp of the TSS, etc. Rings are further divided by chromosomal location of the SNP probes. The wedges are represented as the same size for clarity and are not proportional to either chromosome size or the fraction of the chromosome covered by probes.

After designing and synthesizing the microarray in Example 1 above, the purified proteins p53, NF-kB (p65), TCF4, myc, and AR were tested on the array. TCF4 was only available as a lysate from HEK293 cells and failed to provide any DNA-binding profile. Purified myc required optimization of conditions to obtain a SNP-binding profile. However, the signal-to-noise was still insufficient for complete analysis. Therefore, TCF4 and myc were not studied further and were replaced with two other prostate cancer related transcription factors, Stat3 and ERG. The Stat3 protein was assessed to have low DNA-binding activity and did not yield an acceptable range of signal-to-background on the microarray. Therefore, further analysis was pursued with p53, NF-kB, AR, and ERG.

The master tumor suppressor p53 binds as a tetramer to a repeated 10-bp consensus DNA site separated by a spacer of 0-13 bp. Many mutations that result in cancer, including prostate cancer, act through the p53 pathway (34, 35). In the microarray experiments conducted during the development of embodiments of the technology provided herein, p53 yielded a very strong binding profile with low non-specific binding. p53 was tested in triplicate on the microarray and resulted in a 30-fold greater signal for binding to its highest affinity sequences compared to non-specific sequences. The core DNA-binding motif sequence determined from the array matched well to the known p53 consensus 5'-RRRCW-WGYYY-3' (SEQ ID NO: 1), with R=A/G, Y=C/T, and W=A/T (34).

NF-kB is part of the Rel homology domain family of transcription factors, binds to the consensus sequence 5'-GGGACTTTCC-3' (SEQ ID NO: 2), and plays a role in hormone-independent prostate cancer (36, 37). NF-kB was tested both as a purified p65 homodimer and a p65 (purified)/p50 (cell lysate) heterodimer. The purified p65 homodimer yielded the best signal-to-noise, with an approximately 4-fold greater signal for binding to its consensus sequences compared to non-specific sequences. The DNA binding motif detected from analysis on the triplicate microarrays strongly matched the literature.

AR mediates the activity of dihydrotestosterone (DHT) and controls prostate development and maintenance, thus playing a critical role in prostate cancer including hormone resistance (38, 39). AR binds to DNA with the consensus sequence 5'-GGTACA-NNN-TGTTCT-3' (SEQ ID NO: 3), where N is any nucleotide (40). AR in the presence of DHT recognized its palindromic DNA site of 5-TGTYCT-3' (SEQ ID NO: 4) (Y=C or T) by microarray analysis similar to published results from genome wide binding studies.

ERG is a member of the ETS family of transcription factors and binds to a consensus motif of GGA(A/T) (SEQ ID NO: 5) (41). Fusion of ERG to TMPRSS2 is the most common molecular lesion found in prostate cancer and is present in the majority of prostate cancer samples (42, 43). ERG yielded an excellent signal-to-background (250:1) on the microarray and bound to its expected DNA site of 5'-GGA(A/T)-3' (SEQ ID NO: 5).

In addition to the SNP-SSL analysis, the microarray test SNP data were further analyzed to identify nearby genes, minor allele frequencies (MAFs), and distance to and linkage disequilibrium with their corresponding tag SNPs. These results led to a list of putative causal SNPs, control SNPs, and SNPs in high LD for subsequent analysis (see, e.g., Example 3).

Further analysis compared the microarray results to published reports of ChIP genomic binding sites for the transcription factors. Comparison of the putative functional SNPs (selected in Example 3; see Table 5) with published ChIP-Seq data shows that 9 SNPs intersect with multiple ChIP-Seq peaks from published reports of cell lines or tumor samples. That is, nine of the SNPs selected for subsequent analysis below coincided with genomic binding sites from cell lines or primary tumor samples In sum, experiments were conducted to generate binding profile signatures for each of the purified transcription factors. Further, the SNP microarray results were verified through comparison to previously reported ChIP studies. The SNPs with differentially bound allelic variations identified in this study have been annotated in the genome with catalogued candidate genes. Microarray probes binding profiles were constructed for purified AR, p53, NF-kB (p65), and ERG with some testing of myc, Stat3, and TCF4. SNP-SSL data visualization was developed and integrated into the data analysis.

Example 3—Functional SNPs in Prostate Cancer Patients

During the development of embodiments of the technology provided herein, experiments were conducted to evaluate correlations between the functional SNPs identified in Example 2 with prostate cancer in the human population. First, experiments were conducted to assess the association of the SNPs with prostate cancer in general. Then, experiments were conducted to assess the associated of these SNPs with tumor aggressiveness. The functional SNPs characterized in the experiments described are contemplated to provide a collection of functional SNPs that find use in prostate cancer risk assessment, diagnosis, and personalized therapeutic interventions.

Experiments were conducted to genotype putative functional (e.g., causal) SNPs from genomic regions previously identified by GWAS to be associated with prostate cancer using a case-control patient population. Putative functional (e.g., causal) SNPs were identified by SNP microarrays developed herein as having distinct alleles that result in a significant difference in the binding affinity of a transcription factor to that genomic DNA site (Examples 1 and 2).

Experiments were conducted in collaboration with the Marshfield Clinic, which supplied the archived DNA of 433 prostate cancer patients and 433 control patients matched on body mass index, age, smoking history, and race. Both putative functional (e.g., causal) SNPs and their corresponding GWAS tag SNPs are designed to be genotyped and analyzed to determine if the putative functional (e.g., causal) SNPs provide greater diagnostic utility than the GWAS tag SNPs. Functional SNPs that provide diagnostic power greater than known GWAS tag SNPs provide additional support that the functional SNPs are causal SNPs. In addition to the case-control analysis, the putative functional (e.g., causal) SNPs were examined in prostate cancer patients to determine whether these SNPs assist in differentiating between types of cancer aggressiveness.

The Marshfield Clinic provided pre-existing genotype data for 26 different SNPs. Twenty-five of these SNPs are GWAS tag SNPs associated with prostate cancer. One SNP is a negative control corresponding to the well-known diabetes GWAS tag SNP rs5215. For convenience, the SNPs are identified by a "SNP" number herein, e.g., (SNP1 through SNP26); the standardized rs# and genomic locations given in Table 2.

TABLE 2

Marshfield SNP Descriptions

| Label | rs# | Genomic Region |
|---|---|---|
| Tag_SNP1 | rs2660753 | Chr3: 87 Mb |
| Tag_SNP2 | rs9284813 | Chr3: 87 Mb |
| Tag_SNP3 | rs17181170 | Chr3: 87 Mb |
| Tag_SNP4 | rs7629490 | Chr3: 87 Mb |
| Tag_SNP5 | rs12500426 | Chr4: 94 Mb |
| Tag_SNP6 | rs17021918 | Chr4: 94 Mb |
| Tag_SNP7 | rs6465657 | Chr7: 98 Mb |
| Tag_SNP8 | rs2928679 | Chr8: 24 Mb |
| Tag_SNP9 | rs1512268 | Chr8: 24 Mb |
| Tag_SNP10 | rs1016343 | Chr8: 128 Mb |
| Tag_SNP11 | rs13252298 | Chr8: 128 Mb |
| Tag_SNP12 | rs1456315 | Chr8: 128 Mb |
| Tag_SNP13 | rs16901979 | Chr8: 128 Mb |
| Tag_SNP14 | rs16902094 | Chr8: 128 Mb |
| Tag_SNP15 | rs445114 | Chr8: 128 Mb |
| Tag_SNP16 | rs6983267 | Chr8: 128 Mb |
| Tag_SNP17 | rs1447295 | Chr8: 128 Mb |
| Tag_SNP18 | rs4242382 | Chr8: 128 Mb |
| Tag_SNP19 | rs4242384 | Chr8: 128 Mb |
| Tag_SNP20 | rs7837688 | Chr8: 128 Mb |
| Tag_SNP21 | rs3123078 | Chr10: 51 Mb |
| Tag_SNP22 | rs5215 | Chr11: 17 Mb |
| Tag_SNP23 | rs11228565 | Chr11: 69 Mb |
| Tag_SNP24 | rs1859962 | Chr17: 69 Mb |
| Tag_SNP25 | rs5759167 | Chr22: 43 Mb |
| Tag_SNP26 | rs742134 | Chr22: 43 Mb |

In total, these SNPs cover 9 unique genomic regions, although all tag SNPs in a single genomic region may not necessarily correspond to the same causal variant (e.g., the 11 tag SNPs on chromosome 8 near 128 Mbp may link to more than one independent disease causing SNPs in the region). All 26 SNPs were tested for Hardy-Weinberg Equilibrium (HWE), with only Tag_SNP12 (p=0.048) barely falling below a p-value of 0.05. After adjusting for multiple hypothesis testing correction across the 26 SNPs, none of the SNPs significantly deviated from HWE. Minor allele frequencies range from 0.510 (Tag_SNP16) to 0.969 (Tag_SNP13). Finally, LD was calculated between each pair of SNPs. While there is some minor LD ($r^2<0.33$) for some pairs of SNPs, the vast majority are essentially completely independent. The notable exceptions include the SNP set of Tag_SNP17, Tag_SNP18, Tag_SNP19, and Tag_SNP20 having $r^2$ values of 0.87-0.99. The analysis provides a 26 SNP set with a single negative control of Tag_SNP22 (the diabetes GWAS tag).

These 26 unique GWAS tag SNPs were tested for significance using logistic regression (LR) with the presence of prostate cancer as the dependent variable outcome (disease=1, control=0) and the SNPs as the independent variables. This analysis utilized the entire case-control dataset of 866 patients. Each SNP was considered in 4 different formats including additive (AA=0, AB=1, and BB=2), dominant (AA=0, AB=0, and BB=1), recessive (AA=0, AB=1, BB=1), and genotypic (AA="AA", AB="AB", and BB="BB"). In the genotypic format, the alleles are designed as factors rather than numbers. These four formats account for many of the ways in which a SNP can exert its effect in the cell. Each SNP was tested in each of the four formats in a univariate LR analysis to determine the best format for that SNP.

A final dataset comprising the best format for each SNP was obtained at the completion of the univariate analysis. These best results for each SNP are shown in Table 3. Tag SNPs with a p-value less than 0.1 are indicated by an asterisk in the last column to indicate possible significance.

TABLE 3

Univariate Analysis of Case-Control

| Label | Estimate | OR | p-value | Format | p-value <0.1 |
|---|---|---|---|---|---|
| Tag_SNP1 | 0.283 | 1.327 | 0.0857 | Recessive | * |
| Tag_SNP2 | 0.335 | 1.398 | 0.0282 | Recessive | * |
| Tag_SNP3 | −0.227 | 0.797 | 0.133 | Recessive | |
| Tag_SNP4 | −0.119 | 0.888 | 0.391 | Recessive | |
| Tag_SNP5 | 0.386 | 1.471 | 0.015 | Dominant | * |
| Tag_SNP6 | −0.233 | 0.792 | 0.0883 | Recessive | * |
| Tag_SNP7 | 0.453 | 1.573 | 0.00279 | Recessive | * |
| Tag_SNP8 | −0.162 | 0.850 | 0.346 | Dominant | |
| Tag_SNP9 | 0.418 | 1.519 | 0.00452 | Recessive | * |
| Tag_SNP10 | 0.356 | 1.428 | 0.237 | Dominant | |
| Tag_SNP11 | −0.210 | 0.811 | 0.0465 | Additive | * |
| Tag_SNP12 | 0.515 | 1.674 | 0.0143 | Dominant | * |
| Tag_SNP13 | 0.597 | 1.817 | 0.0399 | Additive | * |
| Tag_SNP14 | 0.135 | 1.145 | 0.315 | Additive | |
| Tag_SNP15 | −0.009 | 0.991 | 0.945 | Recessive | |
| Tag_SNP16 | −0.359 | 0.698 | 0.0209 | Recessive | * |
| Tag_SNP17 | 0.621 | 1.861 | 0.00004 | Additive | * |
| Tag_SNP18 | 0.582 | 1.790 | 8.76E−05 | Additive | * |
| Tag_SNP19 | 0.579 | 1.784 | 0.000105 | Additive | * |
| Tag_SNP20 | 0.424 | 1.528 | 0.00372 | Additive | * |
| Tag_SNP21 | 0.275 | 1.317 | 0.00501 | Additive | * |
| Tag_SNP22 | 0.402 | 1.495 | 0.047 | Dominant | * |
| Tag_SNP23 | 0.224 | 1.251 | 0.0634 | Additive | * |
| Tag_SNP24 | −0.467 | 0.627 | 0.00354 | Dominant | * |
| Tag_SNP25 | 0.134 | 1.143 | 0.164 | Additive | |
| Tag_SNP26 | 1.110 | 3.034 | 0.097 | Dominant | * |

The results from Table 3 show that the majority of GWAS tag SNPs demonstrated at least detectable significance in the Marshfield Clinic prostate cancer case-control population. SNPs with a negative estimate (Odds Ratio <1) are functional SNPs having minor alleles that protect against (e.g., ameliorate) prostate cancer; SNPs with a positive estimate (Odds Ratio >1) are functional SNPs that increase susceptibility to prostate cancer. Only 7 SNPs failed to demonstrate an association—2 SNPs had p-values less than 0.2 and 6 had p-values less than 0.4. Interestingly, the negative control diabetes GWAS tag SNP yielded a p-value of 0.047. Without being bound by theory, this data may reflect the unknown but increasingly supported link between diabetes and cancer (45).

Some tag SNPs from particular genomic regions were significant while others in that same region are not. Without being bound by theory, it is contemplated that not all the tag SNPs in a specific genomic region represent the same disease-causing SNP and thus the experiments are not indicating every disease-causing SNP association in this analysis. This hypothesis was supported by the observation that most of the GWAS tag SNPs in this study are not in high LD with each other, including those in the same genomic regions. Further, it is contemplated this analysis may miss some prostate cancer functional (e.g., causal) SNPs identified in other GWAS analyses because of the homogenous ethnicity of the Marshfield Clinic population or that this initial analysis examined only prostate cancer versus control patients instead of focusing on other specific prostate cancer features such as aggressiveness or PSA levels. Nevertheless, most of the prostate cancer GWAS tag SNPs yielded p-values less than 0.1 in the univariate analysis, which indicates that the Marshfield Clinic population is an accurate reflection of the published literature from other prostate cancer populations and that the sample size is sufficient to identify important disease associations.

In a second analysis, SNPs from Table 2 involved in prostate cancer aggressiveness were analyzed by logistic regression. In this analysis, patients with prostate cancer were divided into high and low Gleason score groups. The distribution of Gleason scores were: 31 patients=2-5; 193 patients=6; 124 patients=7; and 52 patients=8-10. Therefore, the aggressive group comprised patients with a Gleason score of 7 or higher (176 patients) and the non-aggressive group comprised all patients with Gleason score of 6 or lower (224 patients). The remaining 33 prostate cancer patients had no Gleason score associated with them and were removed from further analysis. For this analysis, prostate cancer aggressiveness was the dependent variable (0=lower aggression; 1=higher aggression) and the 26 unique SNPs were the independent variables. The analysis was otherwise performed identically to that described above for the full case-control dataset. The results of the univariate analysis are shown in Table 4 (an asterisk in the last column indicates Tag_SNPs with a p-value <0.1). SNPs with a negative estimate (Odds Ratio <1) have minor alleles that indicate an increased likelihood of lower-aggression prostate cancer while SNPs with a positive estimate (Odds Ratio >1) have minor alleles that indicate an increased likelihood of higher-aggression prostate cancer.

TABLE 4

Univariate Analysis of Prostate Cancer Aggression

| Label | Estimate | OR | p-value | Format | p-value <0.1 |
|---|---|---|---|---|---|
| Tag_SNP1 | 0.347 | 1.415 | 0.138 | recessive | |
| Tag_SNP2 | 0.767 | 2.153 | 0.298 | dominant | |
| Tag_SNP3 | −0.157 | 0.855 | 0.257 | additive | |
| Tag_SNP4AB | 0.459 | 1.582 | 0.0345 | genotype | * |
| Tag_SNP4BB | 0.482 | 1.200 | 0.580 | genotype | |
| Tag_SNP5 | −0.511 | 0.600 | 0.000297 | additive | * |
| Tag_SNP6 | 0.541 | 1.718 | 0.00783 | recessive | * |
| Tag_SNP7 | −0.594 | 0.552 | 0.0114 | recessive | * |
| Tag_SNP8 | −0.248 | 0.780 | 0.0924 | additive | * |
| Tag_SNP9 | −0.270 | 0.763 | 0.291 | dominant | |
| Tag_SNP10 | 0.498 | 1.645 | 0.214 | dominant | |
| Tag_SNP11 | 0.098 | 1.103 | 0.628 | recessive | |
| Tag_SNP12 | 0.262 | 1.300 | 0.196 | recessive | |
| Tag_SNP13 | −0.206 | 0.814 | 0.578 | recessive | |
| Tag_SNP14 | −0.171 | 0.843 | 0.381 | additive | |
| Tag_SNP15 | 0.394 | 1.483 | 0.0549 | recessive | * |
| Tag_SNP16 | 0.263 | 1.301 | 0.262 | dominant | |
| Tag_SNP17 | 0.436 | 1.547 | 0.478 | dominant | |
| Tag_SNP18 | 0.596 | 1.815 | 0.316 | dominant | |
| Tag_SNP19 | 0.823 | 2.277 | 0.195 | dominant | |
| Tag_SNP20 | 0.663 | 1.941 | 0.31 | dominant | |
| Tag_SNP21 | 0.209 | 1.232 | 0.356 | recessive | |
| Tag_SNP22 | −0.164 | 0.849 | 0.553 | dominant | |
| Tag_SNP23 | 0.254 | 1.289 | 0.58 | dominant | |
| Tag_SNP24 | 0.775 | 2.171 | 0.00222 | dominant | * |
| Tag_SNP25 | 0.168 | 1.183 | 0.241 | additive | |
| Tag_SNP26 | 1.530 | 4.618 | 0.0591 | dominant | * |

Some SNPs (e.g., Tag_SNP4 and Tag_SNP15) that are not significant in the full case-control univariate analysis are in this prostate cancer aggression analysis. Conversely, some strong SNPs (e.g., Tag_SNP17 and Tag_SNP21) that are in the case-control analysis are not in this prostate cancer aggression analysis. There are some SNPs (e.g., Tag_SNP5 and Tag_SNP7) that are in both analyses. This result was expected because some SNPs, and presumably some genes, are involved in more than one (e.g., all) stages of the disease, while other SNPs and genes are only involved in initiation or metastasis, for example.

After analyzing pre-existing data from the Marshfield Clinic for tag SNPs, a list of putative functional SNPs (test SNPs) were genotyped by the Marshfield Clinic for comparison with the tag SNP data. Putative functional SNPs were selected based on microarray intensity and level of fold change between alleles; genomic location; proximity to nearby gene transcription start site; and minor allele frequency (MAF). Linkage disequilibrium data from GWAS studies and known overlaps with published ChIP-Seq data for both tumor and cell-line samples were also considered. In total, 20 putative functional (e.g., causal) SNPs and 3 control SNPs were genotyped at the Marshfield Clinic. The prostate cancer associated genes located near the 20 putative functional SNPs are listed (Table 5).

TABLE 5

20 candidate SNPs with nearby genes listed.

| ERG | p53 | p65 | AR |
|---|---|---|---|
| rs3801294, LMTK2 | rs73418011, TSPO | rs138914, TSPO | rs60183675, LMTK2 |
| rs60626102, POUF5F1B | rs12629812, VGLL3 | rs62062347, KCNJ2 | rs9910829, FU37644 |
| rs75485243, PCAT1 | rs2660766, VGLL3 | rs4630241, TIMM23 & PARG | rs7937915, MIR4686 |
| rs8346, SLC25A37 | rs75887480, TTLL1 | | rs1844097, MIR4795 |
| rs10453084, PCAT1 | rs1891702, NUDT11 | | rs2047025, PDLIM5 |
| | rs10825652, TIMM23 & PARG | | rs2452597, PDLIM5 |

The 20 candidate test SNPs that displayed functional binding activity (e.g., a significant intensity difference between SNP alleles on the array for a binding biomolecule (e.g., a transcription factor)) yielded no missing calls when genotyped by the Marshfield Clinic. Of these 20 SNPs, 10 were in high LD with one of the 26 tag SNPs (Table 3) and 10 were not in high LD with any of the tag SNPs that defined the genomic region tiled on the array containing the candidate test SNP. Candidate SNPs in high LD with a tag SNP may represent the true causal determinant driving the association of the tag SNP with prostate cancer. Candidate SNPs that are not in high LD with any tag SNP associated with prostate cancer may represent new causal genetic determinants of prostate cancer not previously known in the art (e.g., not identified in the literature and/or present in SNP databases).

Logistic regression analysis of the full 866 case-control data was performed identically to the first analysis of the tag SNPs, except the independent variables comprised the 20 candidate test SNPs. Each candidate SNP was examined in additive, recessive, dominant, and genotypic formats. In the univariate analysis, 10 candidate test SNPs were identified with a p-value <0.1 (indicated by an asterisk in the last column of Table 6). Three of these significant candidate SNPs (Test_SNP10, Test_SNP11, and Test_SNP23) are not in high LD with any tag SNPs, suggesting these are novel genetic determinants of prostate cancer. Seven of the candidate SNPs (Test_SNP1, Test_SNP2, Test_SNP3, Test_SNP8, Test_SNP9, Test_SNP12, and Test_SNP13) are in high LD with a tag SNP. Of those 7 candidate SNPs, 4 SNPs (Test_SNP1, Test_SNP2, Test_SNP3, and Test_SNP4) have stronger p-values than the tag SNPs with which they have high LD, suggesting that these candidate SNPs may be causal genetic determinants behind the association of the corresponding tag SNPs (Table 7).

TABLE 6

Univariate Analysis of Case-Control

| Label | rs# | Estimate | OR | P-value | Format | Note | p-value < 0.1 |
|---|---|---|---|---|---|---|---|
| Test_SNP1 | rs10453084 | 0.652 | 1.919 | 0.0275 | Additive | LD with Tag_SNP13 | * |
| Test_SNP2AB | rs10825652 | 0.213 | 1.237 | 0.172 | Genotypic | LD with Tag_SNP21 | |
| Test_SNP2BB | | 0.682 | 1.978 | 0.000633 | Genotypic | LD with Tag_SNP24 | * |
| Test_SNP3 | rs12281017 | 0.222 | 1.249 | 0.0645 | Additive | | * |
| Test_SNP4 | rs12629812 | −0.515 | 0.598 | 0.482 | Additive | No Tag in High LD | |
| Test_SNP5 | rs138914 | −0.193 | 0.824 | 0.176 | Recessive | No Tag in High LD | |
| Test_SNP6 | rs1844097 | −0.141 | 0.868 | 0.339 | Recessive | LD with Tag_SNP3 | |
| Test_SNP7 | rs1891702 | 0.184 | 1.202 | 0.186 | Dominant | LD with - | |
| Test_SNP8 | rs2047025 | 0.482 | 1.619 | 0.00402 | Dominant | LD with Tag_SNP5 | * |
| Test_SNP9 | rs2452597 | −0.226 | 0.798 | 0.0343 | Additive | LD with Tag_SNP6 | * |
| Test_SNP10 | rs2660766 | 0.421 | 1.523 | 0.00388 | Recessive | No Tag in High LD | * |
| Test_SNP11 | rs3801294 | 0.418 | 1.519 | 0.00572 | Recessive | No Tag in High LD | * |
| Test_SNP12 | rs4242403 | 0.314 | 1.369 | 0.0279 | Recessive | LD with Tag_SNP9 | * |
| Test_SNP13 | rs4630241 | 0.246 | 1.279 | 0.0118 | Additive | LD with Tag_SNP21 | * |
| Test_SNP14 | rs4988366 | −0.156 | 0.856 | 0.354 | Recessive | LD with Tag_SNP27 | |
| Test_SNP15AB | rs5015755 | 0.307 | 1.359 | 0.047 | Genotypic | Control | * |
| Test_SNP15BB | | −0.234 | 0.791 | 0.563 | Genotypic | | |
| Test_SNP16 | rs5215 | 0.402 | 1.495 | 0.047 | Dominant | Control Diabetes Tag | * |
| Test_SNP17 | rs60183675 | 0.447 | 1.564 | 0.188 | Additive | No Tag in High LD | |
| Test_SNP18 | rs62062347 | −0.227 | 0.797 | 0.115 | Additive | No Tag in High LD | |
| Test_SNP19 | rs7125284 | 0.581 | 1.788 | 0.115 | Dominant | No Tag in High LD | |
| Test_SNP20 | rs75485243 | 0.347 | 1.415 | 0.172 | Additive | No Tag in High LD | |
| Test_SNP21 | rs77779564 | 0.185 | 1.203 | 0.762 | Dominant | No Tag in High LD | |
| Test_SNP22 | rs7792525 | 0.082 | 1.085 | 0.839 | Dominant | Control | |
| Test_SNP23 | rs9910829 | 0.483 | 1.621 | 0.0018 | Recessive | No Tag in High LD | * |

TABLE 7

Comparison between test SNPs and tag SNPs in LD of prostate cancer

| | SNPs from Array | | | Corresponding High LD Tag SNPs | | | Comparison |
|---|---|---|---|---|---|---|---|
| TF | SNP (test) | Odds Ratio | p-value | SNP (tag) | Odds Ratio | p-value | Better SNP |
| ERG | Test_SNP1 | 1.919 | 0.0275 | Tag_SNP13 | 1.817 | 0.0399 | Test SNP |
| p53 | Test_SNP2 | 1.978 | 0.000633 | Tag_SNP21 | 1.317 | 0.00501 | Test SNP |
| ERG | Test_SNP3 | 1.249 | 0.0645 | Tag_SNP24 | 1.251 | 0.0634 | Equal |
| AR | Test_SNP8 | 1.619 | 0.00402 | Tag_SNP5 | 1.471 | 0.015 | Test SNP |
| AR | Test_SNP9 | 0.764 | 0.0487 | Tag_SNP6 | 0.792 | 0.0883 | Test SNP |
| p53 | Test_SNP12 | 1.369 | 0.0279 | Tag_SNP9 | 1.519 | 0.00452 | Tag SNP |
| p65 | Test_SNP13 | 1.279 | 0.0118 | Tag_SNP21 | 1.317 | 0.00501 | Tag SNP |
| ERG | Test_SNP14 | 0.856 | 0.354 | Tag_SNP27 | 3.034 | 0.097 | Tag SNP |
| AR | Test_SNP6 | 0.868 | 0.339 | Tag_SNP3 | 0.797 | 0.133 | Neither |
| p53 | Test_SNP7 | 1.202 | 0.186 | — | — | — | — |

As with the tag SNPs, a second LR analysis using just the 433 prostate cancer cases separated by aggressiveness was performed with the test SNPs as independent variables. Five candidate test SNPs were identified with a p-value <0.1 (Table 8) in a univariate analysis (noted by asterisk in last column). Three of these 5 candidate SNPs (Test_SNP11, Test_SNP18, and Test_SNP23) are not in high LD with any tag SNPs, suggesting these are novel genetic determinants of prostate cancer aggressiveness. Two of the candidate SNPs (Test_SNP8 and Test_SNP9) are in high LD with a tag SNP. Of those 2 candidate SNPs, both have stronger p-values than the tag SNPs with which they are in high LD, suggesting that these candidate SNPs may be the causal genetic determinants behind the association of the corresponding tag SNPs (Table 9).

TABLE 8

Univariate Analysis of Prostate Cancer Aggression

| Label | rs# | Estimate | OR | P-value | Format | Note | p-value < 0.1 |
|---|---|---|---|---|---|---|---|
| Test_SNP1 | rs10453084 | −0.206 | 0.814 | 0.578 | recessive | LD with Tag_SNP13 | |
| Test_SNP2 | rs10825652 | 0.196 | 1.217 | 0.388 | recessive | LD with Tag_SNP21 | |
| Test_SNP3 | rs12281017 | 0.254 | 1.289 | 0.58 | dominant | | |
| Test_SNP4 | rs12629812 | 0.941 | 2.563 | 0.444 | additive | No Tag in High LD | |
| Test_SNP5 | rs138914 | 0.275 | 1.317 | 0.192 | recessive | No Tag in High LD | |
| Test_SNP6 | rs1844097 | −0.179 | 0.836 | 0.401 | recessive | LD with Tag_SNP3 | |
| Test_SNP7 | rs1891702 | 0.143 | 1.154 | 0.162 | additive | LD with - | |
| Test_SNP8 | rs2047025 | −0.518 | 0.596 | 0.000193 | additive | LD with Tag_SNP5 | * |
| Test_SNP9 | rs2452597 | 0.462 | 1.587 | 0.00557 | additive | LD with Tag_SNP6 | * |
| Test_SNP10 | rs2660766 | 0.436 | 1.547 | 0.478 | dominant | No Tag in High LD | |
| Test_SNP11 | rs3801294 | −0.566 | 0.568 | 0.0154 | recessive | No Tag in High LD | * |
| Test_SNP12 | rs4242403 | −0.212 | 0.809 | 0.434 | dominant | LD with Tag_SNP9 | |
| Test_SNP13 | rs4630241 | 0.174 | 1.190 | 0.443 | recessive | LD with Tag_SNP21 | |
| Test_SNP14 | rs4988366 | 0.292 | 1.339 | 0.206 | additive | LD with Tag_SNP27 | |
| Test_SNP15 | rs5015755 | 0.246 | 1.279 | 0.25 | recessive | Control | |
| Test_SNP16 | rs5215 | −0.164 | 0.849 | 0.553 | dominant | Control Diabetes Tag | |
| Test_SNP17 | rs60183675 | −0.476 | 0.621 | 0.316 | additive | No Tag in High LD | |
| Test_SNP18 | rs62062347 | 0.538 | 1.713 | 0.0207 | recessive | No Tag in High LD | * |
| Test_SNP19 | rs7125284 | −0.180 | 0.835 | 0.307 | additive | No Tag in High LD | |
| Test_SNP20 | rs75485243 | −0.150 | 0.861 | 0.687 | recessive | No Tag in High LD | |
| Test_SNP21 | rs77779564 | 0.172 | 1.188 | 0.496 | recessive | No Tag in High LD | |
| Test_SNP22 | rs7792525 | −0.588 | 0.555 | 0.335 | dominant | Control | |
| Test_SNP23 | rs9910829 | −0.778 | 0.459 | 0.0014 | recessive | No Tag in High LD | * |

TABLE 9

Comparison between test SNPs and tag SNPs in LD of prostate cancer aggression

| | SNPs from Array | | | Corresponding High LD Tag SNPs | | | Comparison |
|---|---|---|---|---|---|---|---|
| TF | SNP (test) | OR | P-value | SNP (tag) | OR | P-value | Better SNP |
| ERG | Test_SNP1 | 0.814 | 0.578 | Tag_SNP13 | 0.814 | 0.578 | Neither |
| p53 | Test_SNP2 | 1.217 | 0.388 | Tag_SNP21 | 1.232 | 0.356 | Neither |
| ERG | Test_SNP3 | 1.289 | 0.58 | Tag_SNP24 | 1.289 | 0.58 | Neither |
| AR | Test_SNP8 | 0.596 | 0.00019 | Tag_SNP5 | 0.600 | 0.000297 | Test SNP |
| AR | Test_SNP9 | 1.587 | 0.00557 | Tag_SNP6 | 1.718 | 0.00783 | Test SNP |
| p53 | Test_SNP12 | 0.809 | 0.434 | Tag_SNP9 | 0.763 | 0.291 | Neither |
| p65 | Test_SNP13 | 1.190 | 0.443 | Tag_SNP21 | 1.232 | 0.356 | Neither |
| ERG | Test_SNP14 | 1.339 | 0.206 | Tag_SNP27 | 4.618 | 0.0591 | Tag SNP |
| AR | Test_SNP6 | 0.836 | 0.401 | Tag_SNP3 | 0.855 | 0.257 | Neither |
| p53 | Test_SNP7 | 1.154 | 0.162 | — | — | — | — |

In sum, experiments were conducted to analyze the genotypes at and evaluate 26 tag SNPs and 20 candidate test SNPs for 433 prostate cancer samples compared to an equal number of control patients from Marshfield Clinic. Analysis of the data provided a model of functional (e.g., causal) SNPs for prostate cancer (Tables 3-9).

Current GWAS data from prostate cancer only identify representative SNPs from genomic regions associated with disease. While these studies identify general regions of the genome that are important for disease progression, they fail to provide significant biological insight, and therefore these SNPs have limited diagnostic and therapeutic value. Identification of functional (e.g., causal or ameliorative) SNPs adds valuable biological insight by providing a direct disease target. Since only a small fraction of the human genome encodes proteins, the vast majority of SNPs occur in non-coding regions, such as regulatory sequences. A common function of functional SNPs is that they generate or disrupt binding sites for transcription factors involved in disease and thereby elicit aberrant gene regulation. The experiments described herein identified functional SNPs near GWAS tag SNPs whose differing alleles have a strong effect on the DNA binding of transcription factors involved in prostate cancer.

REFERENCES

1. Kruglyak L, Nickerson D A 2001 Variation is the spice of life. Nat Genet 27:234-236.
2. Hinds D A, Stuve L L, Nilsen G B, Halperin E, Eskin E, Ballinger D G, Frazer K A, Cox D R 2005 Whole genome patterns of common DNA variations in three human populations. Science 307:1072-1079.
3. See SNP website at NCBI
4. Siegel R, Ma J, Zho Z, Jemal A. 2014 Cancer statistics, 2014. CA Cancer J Clin 64:9-29.
5. Mariotto A B, Yabroff K R, Shao Y, Feuer E J, and Brown M L 2011 Projections of the Cost of Cancer Care in the United States: 2010-2020. J Natl Cancer Inst 103:117-128.
6. Perkel J M 2009 Life Science Technologies: Molecular Diagnostics: Personalizing Personalized Medicine. Science 324:815-817.
7. Varghese J S, Easton D F 2010 Genome-wide association studies in common cancers—what have we learnt? Curr Opin Genetics and Development 20:201-209.
8. Eeles R A, Kote-Jarai Z, Giles G G, Al Olama A A, Guy M, Jugurnauth S K, Mulholland S, Leongamornlert D A, Edwards S M, Morrison J, et al. 2008 Multiple newly identified loci associated with prostate cancer susceptibility. Nat Genet 40:316-321.
9. Eeles R A, Kote-Jarai Z, Al Olama A A, Giles G G, Guy M, Severi G, Muir K, Hopper J L, Henderson B E, Haiman C A, et al. 2009 Identification of seven new prostate cancer susceptibility loci through a genome-wide association study. Nat Genet 41:1116-1121. PMCID: PMC2846760.
10. Gudmundsson J, Sulem P, Rafnar, T, Bergthorsson J T, Manolescu A, Gudbjartsson D, Agnarsson B A, Sigurdsson A, Benediktsdottir K R, Blondal T, et al. 2008 Common sequence variants on 2p15 and Xp11.22 confer susceptibility to prostate cancer. Nat Genet 40:281-283.
11. Thomas G, Jacobs K B, Yeager M, Kraft P, Wacholder S. Orr N, Yu K, Chatterjee N, Welch R, Hutchinson A, et al. 2008 Multiple loci identified in a genome-wide association study of prostate cancer. Nat Genet 40:310-315.
12. Venter J C, Adams M D, Myers E W, Li P W, Mural R J, Sutton G G, Smith H O, Yandell M, Evans C A, Holt R A et al. 2001 The sequence of the human genome. Science 291:1304-1351.
13. Gabriel S B, Schaffner S F, Nguyen H, Moore J M, Roy J, Blumenstiel B, Higgins J, DeFelice M, Lochner A, Faggart M, et al. 2002 The structure of haplotype blocks in the human genome. Science 296:2225-2229.
14. Pomerantz M M, Ahmadiyeh N, Jia L, Herman P, Verzi M P, Doddapaneni H, Beckwith C A, Chan J A, Hills A, Davis M, et al. 2009 The 8q24 cancer risk variant rs6983267 shows long-range interaction with MYC in colorectal cancer. Nat Genet 41:882-884. PMCID: PMC2763485.
15. Wright J B, Brown S J, Cole M D 2010 Upregulation of c-MYC in cis through a large chromatin loop linked to a cancer risk-associated single-nucleotide polymorphism in colorectal cancer cells. Mol Cell Biol 30:1411-1420. PMCID: PMC2832500.
16. Ahmadiyeh N, Pomerantz M M, Grisanzio C, Herman P, Jia L, Almendro V, He H H, Brown M, Liu X S, Davis M, et al. 2010 8q24 prostate, breast, and colon cancer risk loci show tissue-specific long-range interaction with MYC. Proc Natl Acad Sci USA 107:9742-9746. PMCID: PMC2906844.
17. Lou H, Yeager M, Li H, Bosquet J G, Hayes R B, Orr N, Yu K, et al 2009 Fine mapping and functional analysis of a common variant in MSMB on chromosome 10q11.2 associated with prostate cancer susceptibility. Proc Natl Acad Sci USA 106: 7933-7938.
18. Hazelett D J, Rhie S K, Gaddis M, Chunli Y, Lakeland D L, Coetzee S G, Henderson B E, et al. 2014 Comprehensive Functional Annotation of 77 Prostate Cancer Risk Loci PLoS genetics 10: e1004102.
19. Duggan D, Zheng S L, Knowlton M, Benitez D, Dimitrov L, et al. (2007) Two genome-wide association studies of aggressive prostate cancer implicate putative prostate tumor suppressor gene DAB2IP. J Natl Cancer Inst 99: 1836-1844.
20. Eeles R A, Kote-Jarai Z, Giles G G, Olama A A, Guy M, et al. (2008) Multiple newly identified loci associated with prostate cancer susceptibility. Nat Genet 40: 316-321.
21. Sun J, Zheng S L, Wiklund F, Isaacs S D, Li G, et al. (2009) Sequence variants at 22q13 are associated with prostate cancer risk. Cancer Res 69: 10-15.
22. Gronberg H (2003) Prostate cancer epidemiology. Lancet 361: 859-864.
23. Gudmundsson J, Sulem P, Gudbjartsson D F, Blondal T, Gylfason A, et al (2009) Genome-wide association and replication studies identify four variants associated with prostate cancer susceptibility. Nat Genet 41: 1122-1126.
24. Eeles R A, Kote-Jarai Z, Al Olama A A, Giles G G, Guy M, et al. (2009) Identification of seven new prostate cancer susceptibility loci through a genomewide association study. Nat Genet 41: 1116-1121.
25. Gudmundsson J, Sulem P, Manolescu A, Amundadottir L T, Gudbjartsson D, et al. (2007) Genome-wide association study identifies a second prostate cancer susceptibility variant at 8q24. Nat Genet 39: 631-637.
26. Gudmundsson J, Sulem P, Rafnar T, Bergthorsson Manolescu A, et al. (2008) Common sequence variants on 2p15 and Xp11.22 confer susceptibility to prostate cancer. Nat Genet 40: 281-283.
27. Hsu F C, Sun J, Wiklund F, Isaacs S D, Wiley K E, et al. (2009) A novel prostate cancer susceptibility locus at 19q13. Cancer Res 69: 2720-2723.
28. Kote-Jarai Z, Easton D F, Stanford J L, Ostrander E A, Schleutker J, et al. (2008) Multiple novel prostate cancer predisposition loci confirmed by an international study: the PRACTICAL Consortium. Cancer Epidemiol Biomarkers Prev 17: 2052-2061.
29. Thomas G, Jacobs K B, Yeager M, Kraft P, Wacholder S, et al. (2008) Multiple loci identified in a genome-wide association study of prostate cancer. Nat Genet 40: 310-315.
30. Yeager M, Chatterjee N, Ciampa J, Jacobs K B, Gonzalez-Bosquet J, et al. (2009) Identification of a new prostate cancer susceptibility locus on chromosome 8q24. Nat Genet 41: 1055-1057.
31. Takata R, Akamatsu S, Kubo M, Takahashi A, Hosono N, et al. (2010) Genome-wide association study identifies five new susceptibility loci for prostate cancer in the Japanese population. Nat Genet 42:751-4.
32. Schumacher F R, Berndt S I, Siddiq A, Jacobs K B, Wang Z, Lindstrom S, et al. (2011) Genome-wide association study identifies new prostate cancer susceptibility loci. Hum Mol Genet. 20:3867-75.
33. Carlson C D, Warren C L, Hauschild K E, Ozers M S, Qadir N, Bhimsaria D, Lee Y, Cerrina F, Ansari A Z 2010 Specificity landscapes of DNA binding molecules elucidate biological function. Proc Natl Acad Sci USA 107: 4544-4549. PMCID: PMC2842033.
34. el-Deiry W S, Kern S E, Pietenpol J A, Kinzler K W, Vogelstein B 1992 Definition of a consensus binding site for p53. Nat Genet 1:45-49.
35. Hollstein M, Sidransky D, Vogelstein B, Harris C C 1991 p53 mutations in human cancers. Science 253:49-53.
36. Lenardo M J, Baltimore D 1989 NF-kappa B: a pleiotropic mediator of inducible and tissue-specific gene control. Cell 58:227-229.
37. Chen C D, Sawyers C L 2002 NF-kappa B activates prostate-specific antigen expression and is upregulated in androgen-independent prostate cancer. Mol Cell Biol 22:2862-2870. PMCID: PMC133743.
38. Taplin M E, Balk S P 2004 Androgen receptor: a key molecule in the progression of prostate cancer to hormone independence. J Cell Biochem 91:483-490.
39. Brooke G N, Bevan C L 2009 The role of androgen receptor mutations in prostate cancer progression. Curr Genomics 10:18-25. PMCID: PMC2699836.
40. Roche P J, Hoare S A, Parker M G 1992 A consensus DNA-binding site for the androgen receptor. Mol Endocrinol 6:2229-2235.
41. Karim F D, Urness L D, Thummel C S, Klemsz M J, McKercher S R, Celada A, Van Beveren C, Maki R A, Gunther C V, Nye J A. 1990 The ETS-domain: a new DNA-binding motif that recognizes a purine-rich core DNA sequence. Genes & Dev 4: 1451-1453.
42. Hermans K G, van Marion R, van Dekken H, Jenster G, van Weerden W M, Trapman J. 2006 TMPRSS2:ERG fusion by translocation or interstitial deletion is highly relevant in androgen-dependent prostate cancer, but is bypassed in late-stage androgen receptor-negative prostate cancer. Cancer Res. 2006 66:10658-63. PMID: 17108102
43. Clark J, Merson S, Jhavar S, Flohr P, Edwards S, Foster C S, Eeles R, Martin F L, Phillips D H, Crundwell M, Christmas T, Thompson A, Fisher C, Kovacs G, Cooper C S 2007 Diversity of TMPRSS2-ERG fusion transcripts in the human prostate. Oncogene 26:2667-2673. PMID 17043636
44. Handel A E, Sandve G K, Disanto G, Handunnetthi L, Giovannoni G, Ramagopalan SV 2013 Integrating multiple oestrogen receptor alpha ChIP studies: overlap with disease susceptibility regions, DNase I hypersensitivity peaks and gene expression. BMC Med Genomics. 6:45. PMID: 24171864
45. Frayling $T_M$, Colhoun H, and Florez J C. A genetic link between type 2 diabetes and prostate cancer Diabetologia 51: 1757-1760.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

What is claimed is:

1. A method for identifying a functional single nucleotide polymorphism (SNP) that modulates binding of a protein to a nucleic acid comprising said functional SNP, said method comprising:
   a) providing a microarray comprising a plurality of probes on a substrate, wherein each probe is a hairpin or double-stranded nucleic acid having a nucleotide sequence comprising a test allele of a SNP and wherein said plurality of probes comprises a probe comprising an allele of rs10453084, a probe comprising an allele of rs10825652, a probe comprising an allele of rs2047025, a probe comprising an allele of rs2660766, a probe comprising an allele of rs4242403, a probe comprising an allele of rs9910829, and a probe comprising an allele of rs62062347;
   b) contacting the microarray with a protein;
   c) measuring a first binding affinity and/or specificity of the protein for a probe having a nucleotide sequence comprising a test allele of a SNP, wherein said first binding affinity and/or specificity is different than a second binding affinity and/or specificity of said protein for a probe having a nucleotide sequence comprising an alternative allele of said SNP; and
   d) identifying said SNP detected to have different first and second binding affinities and/or specificities for the protein to be a functional SNP that modulates binding of said protein to a nucleic acid comprising said functional SNP.

2. The method of claim 1 wherein the test allele of a SNP generates and/or disrupts a genomic binding site for said protein.

3. The method of claim 1 further comprising
   a linking each probe of said plurality of probes to a microarray substrate.

4. The method of claim 1, wherein each test allele of a SNP is present in at least three different hairpin or double-stranded nucleic acid probes.

5. The method of claim 1, wherein said plurality of probes further comprises a probe comprising an allele of rs2660753, rs9284813, rs12500426, rs6465657, rs1512268, rs1456315, rs16901979, rs1447295, rs4242382, rs4242384, rs7837688, rs3123078, rs11228565, rs742134, rs17021918, rs13252298, rs6983267, rs1859962, rs2928679, rs7629490, or rs445114.

6. The method of claim 1 further comprising screening a plurality of test agents to identify an agent that increases or decreases the binding affinity and/or specificity of the protein for the functional SNP.

7. The method of claim 1 further comprising producing a report showing the binding of said protein to said functional SNP, wherein said report comprises a peak height proportional to a binding affinity of the protein to said functional SNP and a peak position indicating chromosomal genomic location of said functional SNP and/or a genomic distance of said functional SNP to the transcription start site of the nearest gene.

8. The method of claim 1, wherein the protein binds directly to the test allele and/or to the alternative allele of a SNP.

9. The method of claim 1 wherein said protein is a transcription factor.

10. The method of claim 1 further comprising reporting said protein and said test allele of a SNP as being associated with prostate cancer.

11. The method of claim 1 wherein said protein is a transcription factor selected from the group consisting of androgen receptor (AR), p53, nuclear factor kappa-light-chain-enhancer of activated B cells (NF-kB), myc, TCF4, ERG, and Stat3.

12. The method of claim 1 wherein said plurality of probes further comprises a probe comprising an allele of a SNP from a genomic region comprising a SNP selected from the group consisting of rs2660753, rs9284813, rs12500426, rs6465657, rs1512268, rs1456315, rs16901979, rs1447295, rs4242382, rs4242384, rs7837688, rs3123078, rs11228565, rs742134, rs17021918, rs13252298, rs6983267, rs1859962, rs2928679, rs7629490, and rs445114.

13. The method of claim 1 wherein said alternative allele is a single-nucleotide change or an indel.

14. The method of claim 1 wherein said test allele is a mutant allele.

15. The method of claim 1 wherein said alternative allele is a wild-type allele.

16. The method of claim 1 wherein said alternative allele is a mutant allele.

* * * * *

SEQUENCE LISTING

<160> NUMBER OF SEQ ID NOS: 12

<210> SEQ ID NO 1
<211> LENGTH: 10
<212> TYPE: DNA
<213> ORGANISM: Artificial sequence
<220> FEATURE:
<223> OTHER INFORMATION: Consensus sequence
<220> FEATURE:
<221> NAME/KEY: misc_feature
<222> LOCATION: (1)..(3)
<223> OTHER INFORMATION: A or G
<220> FEATURE:
<221> NAME/KEY: misc_feature
<222> LOCATION: (5)..(6)
<223> OTHER INFORMATION: A or T
<220> FEATURE:
<221> NAME/KEY: misc_feature
<222> LOCATION: (8)..(10)
<223> OTHER INFORMATION: C or T

<400> SEQUENCE: 1 rrrcwwgyyy                                                              10

<210> SEQ ID NO 2
<211> LENGTH: 10
<212> TYPE: DNA
<213> ORGANISM: Artificial sequence
<220> FEATURE:
<223> OTHER INFORMATION: Consensus sequence

<400> SEQUENCE: 2
gggactttcc                                                              10

<210> SEQ ID NO 3
<211> LENGTH: 15
<212> TYPE: DNA
<213> ORGANISM: Artificial sequence
<220> FEATURE:
<223> OTHER INFORMATION: Consensus sequence
<220> FEATURE:
<221> NAME/KEY: misc_feature
<222> LOCATION: (7)..(9)
<223> OTHER INFORMATION: any nucleotide

<400> SEQUENCE: 3
ggtacannnt gttct                                                        15

<210> SEQ ID NO 4
<211> LENGTH: 6
<212> TYPE: DNA
<213> ORGANISM: Artificial sequence
<220> FEATURE:
<223> OTHER INFORMATION: Consensus sequence
<220> FEATURE:
<221> NAME/KEY: misc_feature
<222> LOCATION: (4)..(4)
<223> OTHER INFORMATION: C or T

<400> SEQUENCE: 4 tgtyct                                                                   6

<210> SEQ ID NO 5
<211> LENGTH: 4
<212> TYPE: DNA
<213> ORGANISM: Artificial sequence
<220> FEATURE:
<223> OTHER INFORMATION: Consensus sequence
<220> FEATURE:
<221> NAME/KEY: misc_feature

```
<222> LOCATION: (4)..(4)
<223> OTHER INFORMATION: A or T

<400> SEQUENCE: 5 ggaw                                                                        4

<210> SEQ ID NO 6
<211> LENGTH: 66
<212> TYPE: DNA
<213> ORGANISM: Artificial sequence
<220> FEATURE:
<223> OTHER INFORMATION: Synthetic construct

<400> SEQUENCE: 6
gctgacggtc attcgatgaa cgtcaatgcg ttcctacgca ttgacgttga tcgaatgacc          60
gtcagc                                                                     66

<210> SEQ ID NO 7
<211> LENGTH: 66
<212> TYPE: DNA
<213> ORGANISM: Artificial sequence
<220> FEATURE:
<223> OTHER INFORMATION: Synthetic construct

<400> SEQUENCE: 7
gctgacggtc attcggtgaa cgtcaatgcg ttcctacgca ttgacgttga ccgaatgacc          60
gtcagc                                                                     66

<210> SEQ ID NO 8
<211> LENGTH: 51
<212> TYPE: DNA
<213> ORGANISM: Artificial sequence
<220> FEATURE:
<223> OTHER INFORMATION: Synthetic construct

<400> SEQUENCE: 8
ggtcatatcc gctgacggtc attcgatgaa cgtcaatgcg tattcgcgca a                   51

<210> SEQ ID NO 9
<211> LENGTH: 51
<212> TYPE: DNA
<213> ORGANISM: Artificial sequence
<220> FEATURE:
<223> OTHER INFORMATION: Synthetic construct

<400> SEQUENCE: 9
ttgcgcgaat acgcattgac gttgatcgaa tgaccgtcag cggatatgac c                   51

<210> SEQ ID NO 10
<211> LENGTH: 66
<212> TYPE: DNA
<213> ORGANISM: Artificial sequence
<220> FEATURE:
<223> OTHER INFORMATION: Synthetic construct

<400> SEQUENCE: 10
ggtcatatcc gctgacggtc attcgatgaa ctcctgttga tcgaatgacc gtcagcggat          60
atgacc                                                                     66

<210> SEQ ID NO 11
<211> LENGTH: 66
<212> TYPE: DNA
<213> ORGANISM: Artificial sequence
<220> FEATURE:
```

```
<223> OTHER INFORMATION: Synthetic construct

<400> SEQUENCE: 11
gctgacggtc attcgatgaa cgtcaatgcg ttcctacgca ttgacgttga tcgaatgacc      60
gtcagc                                                                 66

<210> SEQ ID NO 12
<211> LENGTH: 66
<212> TYPE: DNA
<213> ORGANISM: Artificial sequence
<220> FEATURE:
<223> OTHER INFORMATION: Synthetic construct

<400> SEQUENCE: 12
attcgatgaa cgtcaatgcg tattcgcgca atcctttgcg cgaatacgca ttgacgttga      60
tcgaat                                                                 66
```